(12) United States Patent
Viens et al.

(10) Patent No.: US 11,717,451 B2
(45) Date of Patent: Aug. 8, 2023

(54) FLUID MANAGEMENT LAYER FOR AN ABSORBENT ARTICLE

(71) Applicant: The Procter & Gamble Company, Cincinnati, OH (US)

(72) Inventors: Gerard A. Viens, Wyoming, OH (US); Jacquelyn Harris, Cincinnati, OH (US); Carlos Domingo Naranjo Martin, Frankfurt (DE); Alejandro Navarro, Idstein (DE)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 793 days.

(21) Appl. No.: 16/831,851

(22) Filed: Mar. 27, 2020

(65) Prior Publication Data

US 2020/0306099 A1 Oct. 1, 2020

Related U.S. Application Data

(60) Provisional application No. 62/826,178, filed on Mar. 29, 2019.

(51) Int. Cl.
*A61F 13/15* (2006.01)
*A61F 13/537* (2006.01)
(Continued)

(52) U.S. Cl.
CPC ........ *A61F 13/42* (2013.01); *A61F 13/15203* (2013.01); *A61F 13/53708* (2013.01);
(Continued)

(58) Field of Classification Search
CPC .............. A61F 13/15203; A61F 13/537; A61F 13/53708; A61F 13/53713;
(Continued)

(56) References Cited

U.S. PATENT DOCUMENTS

| 5,607,414 A | 3/1997 | Richards |
| 5,810,796 A | 9/1998 | Kimura |

(Continued)

FOREIGN PATENT DOCUMENTS

| CN | 1193269 A | 9/1998 |
| CN | 1874742 A | 12/2006 |

(Continued)

OTHER PUBLICATIONS

PCT Search Report and Written Opinion (PCT/US2020/025126) dated May 26, 2020.
(Continued)

*Primary Examiner* — Catharine L Anderson
(74) *Attorney, Agent, or Firm* — William E. Gallagher; George H. Leal

(57) ABSTRACT

A fluid management layer having a basis weight of between about 40 grams per square meter (gsm) and about 120 gsm is described. The fluid management layer has a plurality of absorbent fibers, a plurality of stiffening fibers and a plurality of resilient fibers, wherein the absorbent fibers are present at about 20 percent to about 75 percent by weight, and wherein the integrated, carded, staple fiber, nonwoven has a first side and a second side, and wherein there is a higher number of absorbent fibers on the first side or second side versus the other.

20 Claims, 10 Drawing Sheets

(51) Int. Cl.
*A61F 13/42* (2006.01)
*A61F 13/53* (2006.01)
*A61F 13/84* (2006.01)

(52) U.S. Cl.
CPC .............. *A61F 2013/15292* (2013.01); *A61F 2013/15357* (2013.01); *A61F 2013/15406* (2013.01); *A61F 2013/15422* (2013.01); *A61F 2013/15447* (2013.01); *A61F 2013/530233* (2013.01); *A61F 2013/8497* (2013.01)

(58) Field of Classification Search
CPC ............ A61F 13/53717; A61F 13/5376; A61F 13/538; A61F 2013/15292; A61F 2013/153; A61F 2013/15406; A61F 2013/15447; A61F 2013/5383; A61F 2013/5386; A61F 2013/8497
See application file for complete search history.

(56) References Cited

U.S. PATENT DOCUMENTS

| | | | |
|---|---|---|---|
| 5,997,980 | A | 12/1999 | Matoba |
| 6,060,638 | A | 5/2000 | Paul |
| 6,884,494 | B1 | 4/2005 | Curro |
| 7,597,689 | B2 | 10/2009 | Hoffmann |
| 8,389,427 | B2 | 3/2013 | Gustafsson |
| 10,307,309 | B2 | 6/2019 | Viens |
| 10,532,123 | B2 | 1/2020 | Viens |
| 2003/0220048 | A1 | 11/2003 | Toro |
| 2004/0018795 | A1 | 1/2004 | Viazmensky |
| 2004/0087924 | A1 | 5/2004 | Sroda |
| 2005/0033253 | A1 | 2/2005 | Fuchs |
| 2005/0136773 | A1 | 6/2005 | Yahiaoui |
| 2006/0058762 | A1 | 3/2006 | Yang |
| 2008/0113574 | A1 | 5/2008 | Neron |
| 2008/0119806 | A1 | 5/2008 | Nguyen |
| 2012/0041410 | A1 | 2/2012 | Ueda |
| 2012/0160400 | A1 | 6/2012 | Calewarts et al. |
| 2014/0005622 | A1 | 1/2014 | Wirtz |
| 2014/0343523 | A1 | 11/2014 | Viens |
| 2015/0250654 | A1 | 9/2015 | Pernot |
| 2015/0351976 | A1 | 12/2015 | Viens |
| 2016/0213532 | A1 | 7/2016 | Takahashi |
| 2017/0119597 | A1* | 5/2017 | Bewick-Sonntag ........................ A61F 13/532 |
| 2018/0098889 | A1 | 4/2018 | Hardie |
| 2018/0098893 | A1 | 4/2018 | Viens |
| 2019/0247244 | A1 | 8/2019 | Viens |
| 2020/0101191 | A1 | 4/2020 | Viens |

FOREIGN PATENT DOCUMENTS

| | | |
|---|---|---|
| CN | 102164569 A | 8/2011 |
| CN | 105658189 A | 6/2016 |
| EP | 1504739 A1 | 2/2005 |
| EP | 2692321 A1 | 2/2014 |
| JP | H10273884 A | 10/1998 |
| JP | 2008106383 A | 5/2008 |
| WO | WO9723182 A1 | 7/1997 |
| WO | WO0134085 A1 | 5/2001 |
| WO | WO2008066417 A1 | 6/2008 |

OTHER PUBLICATIONS

All Office Actions for U.S. Appl. No. 16/831,862, filed Mar. 27, 2020.

* cited by examiner

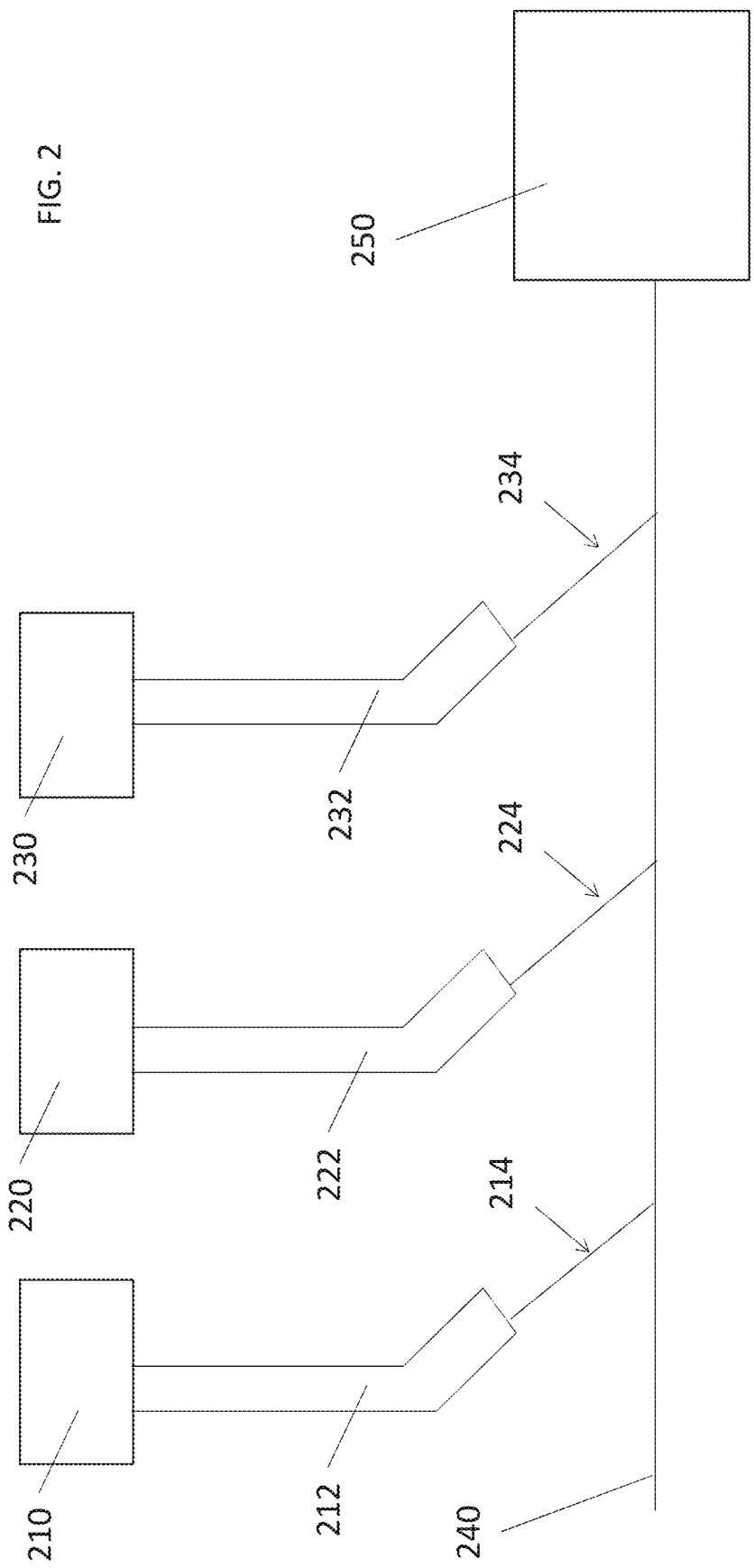

FLUID MANAGEMENT LAYER FOR AN ABSORBENT ARTICLE

TECHNICAL FIELD

The present disclosure generally relates to an absorbent layer for a disposable absorbent article having carded staple fiber nonwovens having improved performance characteristics.

BACKGROUND

Disposable absorbent articles such as feminine hygiene products, taped diapers, pant-type diapers and incontinence products are designed to absorb fluids from the wearer's body. Users of such disposable absorbent articles have several concerns. One of the biggest concerns pertains to leakage of excreted fluid from the absorbent article. Leakage from products like catamenial pads, diapers, sanitary napkins, and incontinence pads is a significant concern.

To address the concern of leakage, many manufacturers seek to reassure consumers regarding their respective products leakage capacity. Some manufacturers may choose a combination of methods to do this. For example, advertising can be utilized to show the volume of liquid that the absorbent article can retain may be shown. And, some manufacturers have begun to provide visual signals visible from a wearer-facing surface of the absorbent article.

These visual signals can be utilized to highlight aspects of the absorbent article which may normally be hidden to the consumer. For example, the full extent of the absorbent system within the absorbent article may not be easily discernable to the naked eye. However, the visual signal can be provided to help persuade the consumer that adequate absorbent capacity exists.

Providing visual signals visible from the wearer-facing surface of the absorbent article can be problematic. For example, where the visual signal is provided on the topsheet of the absorbent article, the issue of rub-off is of substantial concern. Specifically, ink may bleed onto the skin of the wearer which can negatively impact the impression of the article with the consumer as well as lead to negative publicity for the absorbent article and the manufacturer thereof.

Providing the visual signal on layers beneath the wearer-facing surface can have its challenges as well. For example, the web upon which ink is being deposited should be substantial enough to withstand ink blow through. Ink blow through occurs when ink "blows" through the web and onto a carrier belt. The ink contaminates the belt and can lead to quality defects in the visual signal for subsequent absorbent articles. Additionally, the web upon which ink is being deposited should be substantial enough such that visual signal appropriately registers with online visual systems. Specifically, where printed webs are too porous, online visual systems may treat open areas in the webs as defects thereby triggering a false positive. This could lead to slowed production time as well as a substantial amount of lost revenue.

As such, there is a need to create an absorbent article having a visual signal that avoids triggering false positives in online visual systems and reduces the likelihood of ink blow through.

SUMMARY

Absorbent articles of the present disclosure comprise a topsheet, a backsheet, and an absorbent core disposed between the topsheet and the backsheet. A fluid management layer is disposed between the topsheet and the absorbent core. A visual signal is printed onto the fluid management layer, wherein the visual signal is visible through the topsheet.

The fluid management layer comprises a carded-staple fiber nonwoven material comprising a plurality of fibers. The plurality of fibers in combination reduce the likelihood of false positives from visual systems inspecting visual signals and reduce the likelihood of ink blow-through. In one specific execution, a fluid management layer comprises an integrated, carded, nonwoven having a basis weight of between about 40 grams per square meter (gsm) and about 120 gsm, the fluid management layer comprising a plurality of absorbent fibers, a plurality of stiffening fibers and a plurality of resilient fibers, wherein the absorbent fibers comprise from about 20 percent to about 75 percent by weight, wherein the stiffening fibers comprise bi-component fibers at about 10 percent to about 40 percent by weight, wherein the resilient fibers comprise from about 20 percent to about 40 percent by weight, wherein the fluid management layer has a first side and a second side, and wherein there is a higher number of absorbent fibers on the first side or second side versus the other.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 2 is a schematic representation of a process which can be utilized to construct fluid management layer of the present disclosure;

DETAILED DESCRIPTION

Figure 1A:
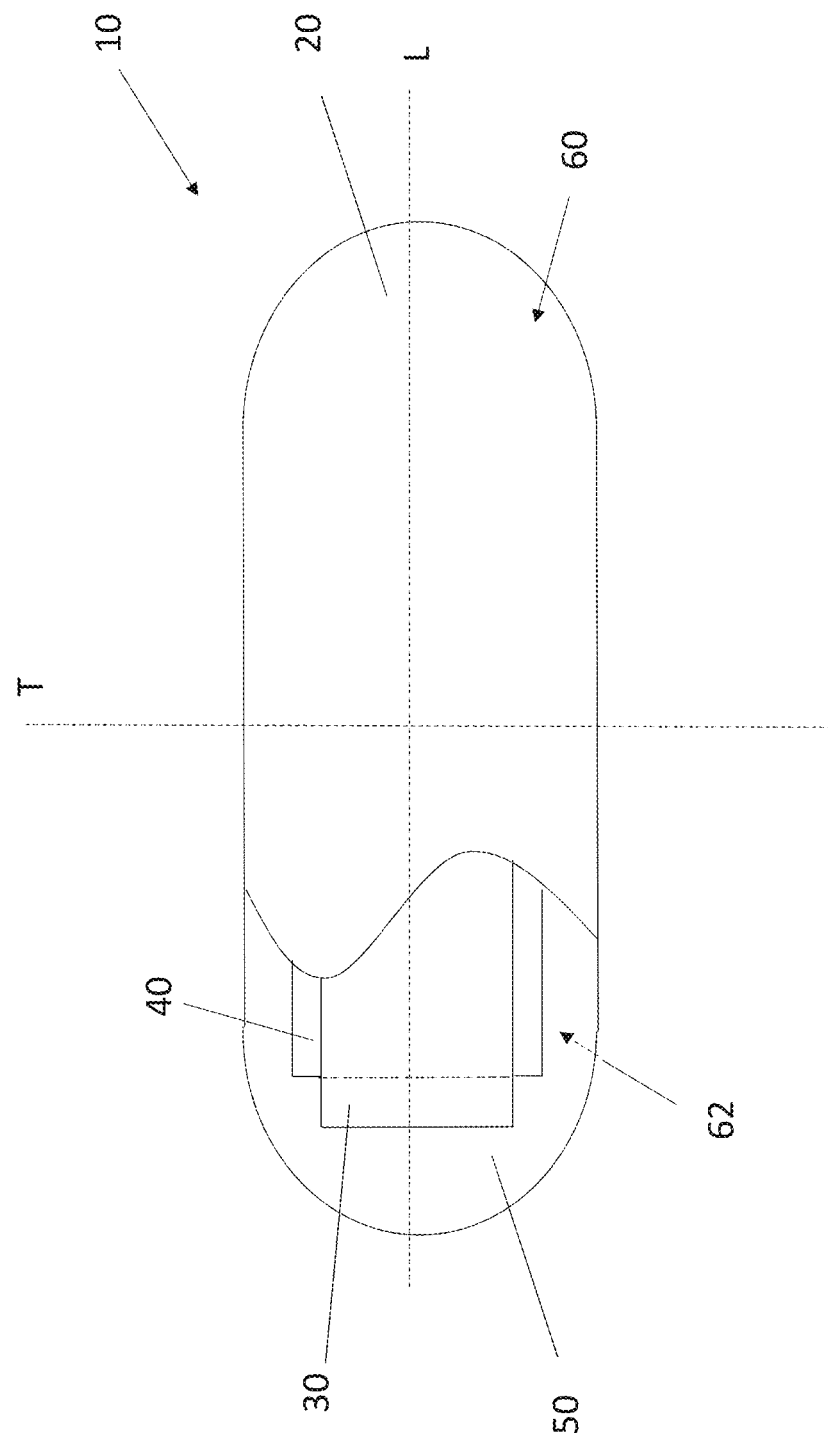
FIG. 1A is a schematic representation of a disposable absorbent article constructed in accordance with the present disclosure.

As used herein, the following terms shall have the meaning specified thereafter:

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments (e.g., liners, pads and briefs) and/or feminine hygiene products.

The "longitudinal" direction is a direction running parallel to the maximum linear dimension, typically the longitudinal axis, of the article and includes directions within 45° of the longitudinal direction. "Length" of the article or component thereof, when used herein, generally refers to the size/distance of the maximum linear dimension, or typically to the size/distance of the longitudinal axis, of an article or part thereof.

The "lateral" or "transverse" direction is orthogonal to the longitudinal direction, i.e. in the same plane of the majority of the article and the longitudinal axis, and the transverse direction is parallel to the transverse axis. "Width" of the article or of a component thereof, when used herein, refers to the size/distance of the dimension orthogonal to the longitudinal direction of the article or component thereof, i.e. orthogonal to the length of the article or component thereof, and typically it refers to the distance/size of the dimension parallel of the transverse axis of the article or component.

The "Z-direction" is orthogonal to both the longitudinal and transverse directions.

"Machine Direction" or "MD" as used herein means the direction parallel to the flow of the carded staple fiber nonwoven through the nonwoven making machine and/or absorbent article product manufacturing equipment.

"Cross Machine Direction" or "CD" as used herein means the direction parallel to the width of the carded staple fiber nonwoven making machine and/or absorbent article product manufacturing equipment and perpendicular to the machine direction.

The term "integrated" as used herein is used to describe fibers of a nonwoven material which have been intertwined, entangled, and/or pushed/pulled in a positive and/or negative Z-direction (direction of the thickness of the nonwoven material). Some exemplary processes for integrating fibers of a nonwoven web include spunlacing and needlepunching. Spunlacing uses a plurality of high-pressure water jets to entangle fibers. Needlepunching involves the use of needles to push and/or pull fibers to entangle them with other fibers in the nonwoven. And this type of integration obviates the need for adhesive or a binding agent to hold the fibers of the fluid management layer together.

The term "carded" as used herein is used to describe structural features of the fluid management layers described herein. A carded nonwoven utilizes fibers which are cut to a specific length, otherwise known as "staple length fibers." Staple length fibers may be any suitable length. For example, staple length fibers may have a length of up to 120 mm or may have a length as short as 10 mm. However, if a particular group of fibers are staple length fibers, for example viscose fibers, then the length of each of the viscose fibers in the carded nonwoven is predominantly the same, i.e. the staple length. It is worth noting that where additional staple fiber length fiber types are included, for example, polypropylene fibers, the length of each of the polypropylene fibers in the carded nonwoven is also predominantly the same. But, the staple length of the viscose and the staple length of the polypropylene may be different.

In contrast, continuous filaments such as by spunbonding or meltblowing processes, do not create staple length fibers. Instead, these filaments are of an indeterminate length and are not cut to a specific length as noted regarding their staple fiber length counterparts.

A fluid management layer comprising a carded, integrated, nonwoven as disclosed herein can be used in a variety of disposable absorbent articles, but is particularly useful in diapers, feminine hygiene products and incontinence products such as sanitary napkins and incontinence pads. The fluid management layer of the present disclosure are particularly effective when a visual signal is printed thereon. A schematic cross-section of an exemplary absorbent article is shown in FIG. 1A.

Where the fluid management layer comprises a visual signal, the inventors have found that the opacity of the nonwoven material impacted the likelihood of triggering false positives in visual systems. Additionally, the inventors have found that the opacity also correlates to the amount of ink blow through during the printing process. Ink blow through is the amount of ink which passes through the nonwoven material during the printing process. In general, ink blow through is not seen as a positive occurrence. Rather, ink blow through can contaminate the web handling equipment and leave trace amounts of ink on subsequent webs where ink may not be desired. The opacity of the integrated, carded, nonwovens of the present disclosure are discussed in additional detail hereafter.

Figure 1B:
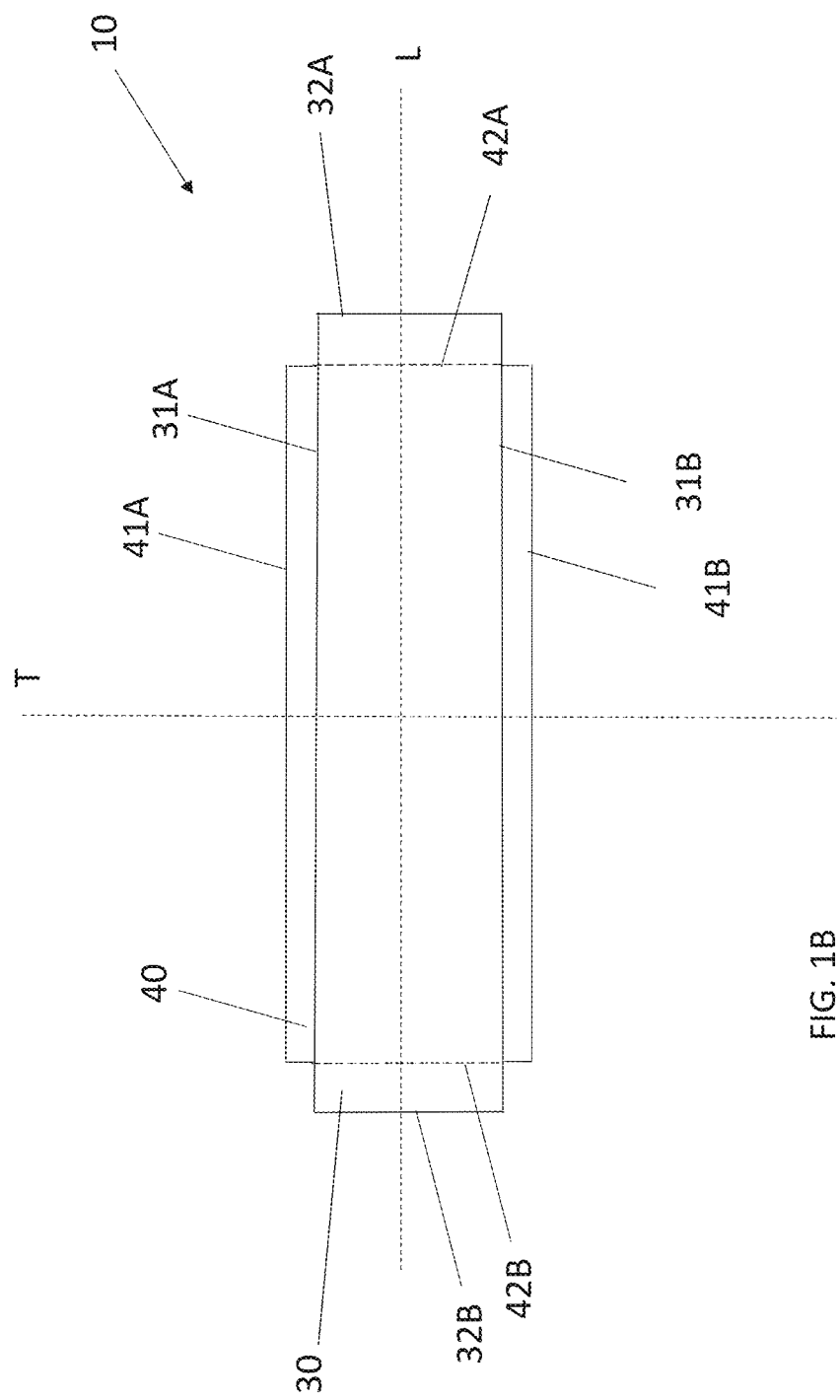
FIG. 1B is a schematic representation of an absorbent system of the disposable absorbent article shown in FIG. 1A.
Figure 3:
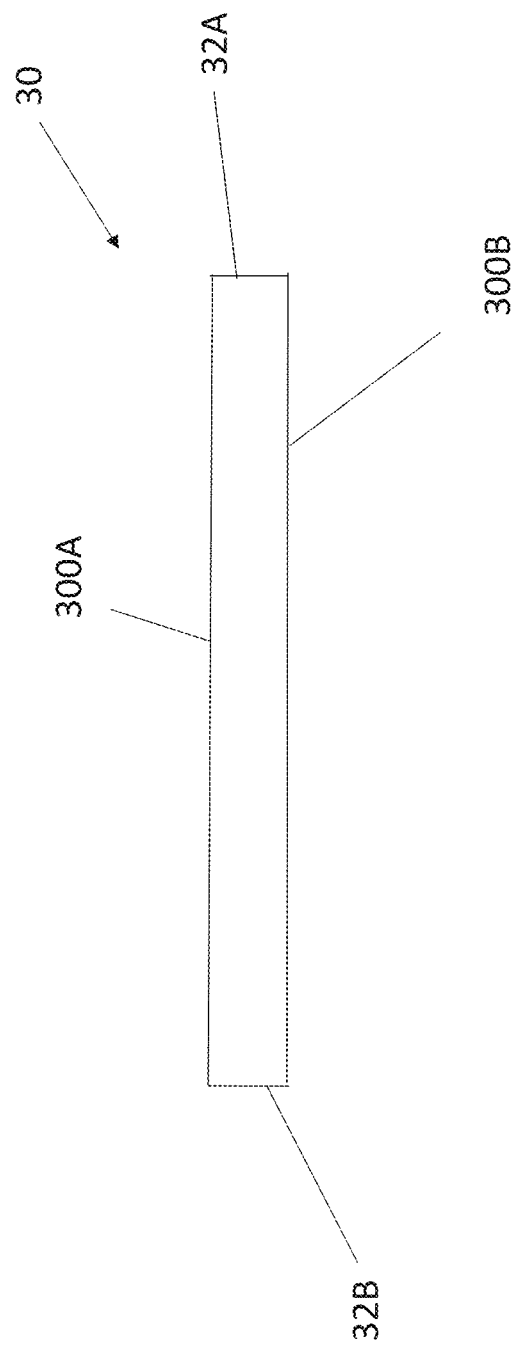
FIG. 3 is a schematic representation of an elevation view of a fluid management layer constructed in accordance with the present disclosure.

Referring to FIGS. 1A and 1B, absorbent articles 10 in accordance with the present disclosure comprise a topsheet 20, a backsheet 50, and an absorbent core 40 disposed between the topsheet 20 and the backsheet 50. A fluid management layer 30 is disposed between the topsheet 20 and the backsheet 50, and in some specific instances between the topsheet 20 and the absorbent core 40. The absorbent article has a wearer-facing surface 60 and an opposing garment-facing surface 62. The wearer-facing surface 60 primarily comprises the topsheet 20 while the garment-facing surface 62 primarily comprises the backsheet 50. Additional components may be included in either the wearer-facing surface 60 and/or the garment-facing surface 62. For example, where the absorbent article is an incontinent pad, a pair of barrier cuffs which extend generally parallel to a longitudinal axis L of the absorbent article 10, may also form a portion of the wearer-facing surface 60. Similarly, a fastening adhesive may be present on the backsheet 50 and form a portion of the garment-facing surface 62 of the absorbent article.

The fluid management layer 30 comprises opposing end edges 32A and 32B which may extend generally parallel to a transverse axis T. And, the fluid management layer 30 comprises side edges 31A and 32B which may extend generally parallel to the longitudinal axis L. Similarly, the absorbent core 40 comprises opposing end edges 42A and 42B which may extend generally parallel to the transverse axis T. And, the absorbent core 40 may comprise side edges 41A and 41B which extend generally parallel to the longitudinal axis L.

As shown, each of the end edges 32A and 32B of the fluid management layer 30 may be disposed longitudinally outboard of the absorbent core 40. However, this is not necessarily required. For example, the end edges 32A and/or 32B may be coextensive with the absorbent core 40 or the end edges 32A and/or 32B may be disposed longitudinally inboard of the end edges 42A and/or 42B of the absorbent core 40.

Similarly, the side edges 31A and/or 31B may be disposed transversely outboard of the side edges 41A and/or 41B of the absorbent core 40. Or, the side edges 31A and/or 31B may be coextensive with the side edges 41A and/or 41B of the absorbent core 40.

As noted previously, the fluid management layer 30 is an integrated, carded, nonwoven material. A schematic representation of a carding and integrating process suitable for creating the fluid management layer 30 of the present disclosure is provided in FIG. 2. As shown, a plurality of carding machines 210, 220, and 230 may each create a carded nonwoven web, e.g. 214, 224, and 234, respectively, which is transferred to a carrier belt 240. Each of the carded nonwoven webs 214, 224, and 234, may be provided to the carrier belt 240 via a web chute 212, 222, 232, respectively. It is also worth noting that after the carded nonwoven 214 is deposited on the carrier belt 240, the carded nonwoven 224 is then deposited on the first carded nonwoven 214 on the carrier belt 240. Similarly, the third carded nonwoven web 234 deposited on the second carded nonwoven 224 and the first carded nonwoven 214 on the carrier belt 240. Subsequently, each of the first, second, and third carded nonwoven webs 214, 224, and 234 are then provided to an integration process 250 which utilizes either needles and/or high pressure water streams to entangle the fibers of the first, second, and third carded nonwoven webs. Both carding and integration processes are well known in the art.

It is worth noting that with the arrangement provided in schematic diagram of FIG. 2, a wide variety of configurations for a fluid management layer may be achieved. However, it is important that the fluid management layer of the present disclosure have adequate openness to allow for quick acquisition of fluid. In addition, to quick fluid acquisition, the fluid management layers of the present disclosure should ensure good fluid distribution to the absorbent core. The inventors have found that the more efficient the fluid management layer is regarding fluid distribution to the absorbent core, the less the stain intensity and/or size of the stain that is visible through the topsheet. Unfortunately, the openness of the fluid management layer can also lead to problems as visions systems may see open areas as defects in a visual signal. With this in mind, the carded webs, i.e. 214, 224, and/or 234, may be different from one another. For example, one of the carded webs may comprise a different fiber blend than the others. Specifically, assuming the first carded web would be closest to the wearer-facing surface in an absorbent article, the fiber selection for the first carded web 214 may be such that there is more openness associated with this web. The second carded web 224 may be similarly configured. In contrast, the third carded web 234 may be configured to reduce the likelihood of false positives by vision systems which "see" open areas as defects. The third carded web 234 may be configured to effectively distribute liquid insults to the subjacent absorbent core—in conjunction or independent of the reduction of false positives. Where two cards differ in their fiber makeup, the nonwoven is termed heterogeneous. Where all cards have the same fiber blend, the nonwoven is termed homogeneous.

If the first carded web 214 and the second carded web 224 comprise the same fiber blend, then the fluid management layers of the present disclosure may be processed via two cards instead of three. However, such processing would potentially slow the production of the first carded layer 214 which would comprise a much higher basis weight than that of the third carded web 234.

Referring now to FIGS. 1A-3, the first carded nonwoven 214, the second carded nonwoven 224 (optional, as previously mentioned), and the third carded nonwoven 234 are integrated. Once they are integrated, they cannot be manually separated—at least not without substantial effort and time. Each carded nonwoven web forms a stratum in the overall fluid management layer 30. Each stratum can maintain its unique properties for at least a portion of the stratum along the z-direction, even when integrated into a larger fluid management layer 30. The fluid management layer 30 provides capillary suction to "pull" fluid through the topsheet 20, which is competing for trickle/low flow conditions. The fluid management layer 30 also can contain a gush by providing distribution functions to efficiently utilize the absorbent core 40, as well as provide intermediate storage until the absorbent core 40 can accept fluid.

The fluid management layer 30 has a first surface 300A and an opposing second surface 300B. Between the first surface 300A and the second surface 300B, the fluid distribution layer 30 comprises of two or more strata along the Z-direction. The fluid management layer 30 can have a basis weight of up to 120 grams per square meter (gsm); or a basis weight of up to 100 gsm; or a basis weight in the range of about 30 gsm to about 120 gsm; or in the range of about 40 gsm to about 100 gsm; or in the range of about 45 gsm to about 70 gsm; or in the range of about 50 gsm to about 55 gsm, including any values within these ranges and any ranges created thereby. In one specific example, the fluid management layer 30 may have a basis weight of about 50 gsm to about 75 gsm.

The fluid management layer 30 can have a caliper of between 0.6 millimeters (mm) and 1.5 mm including any values within these ranges and any ranges created thereby.

Due to the fiber integration, the fluid management layer 30 does not require adhesives or latex binders for stability. Additionally, the carded staple fiber nonwoven of the fluid management layer can be manufactured from an assortment of suitable fiber types that produce the desired performance characteristics. For example, the fluid management layer 30 may comprise a combination of stiffening fibers, absorbent fibers and resilient fibers.

In order to enhance the stabilizing effect of the integration, crimped fibers may be utilized. As discussed in additional detail below, the fluid management layer of the present disclosure may comprise absorbent fibers, stiffening fibers, and resilient fibers. One or more of these fibers may be crimped prior to integration. For example, where synthetic fibers are utilized, these fibers may be mechanically crimped via intermeshing teeth. And for the absorbent fibers, these fibers may be mechanically crimped and/or may have a chemically induced crimp due to the variable skin thickness formed during creation of the absorbent fibers.

Overall the fluid management layer may comprise from about 20 percent to about 75 percent by weight, from about 25 percent to about 60 percent by weight, from about 30 percent to about 50 percent by weight, specifically including any values within these ranges and any ranges created thereby of absorbent fibers. In one specific example, the fluid management layer 30 may comprise from about 40 percent to about 50 percent by weight absorbent fibers.

Similarly, overall the fluid management layer 30 may comprise from about 10 percent to about 50 percent, from about 13 percent to about 40 percent, from about 20 percent to about 35 percent, from about 25 percent to about 30 percent by weight of resilient fibers, specifically reciting all values within these ranges and any ranges created thereby. In one specific example, the fluid management layer 30 may comprise from about 26 percent to about 33 percent by weight resilient fibers.

And, the fluid management layer 30 may comprise from about 1 percent to about 50 percent, from about 10 percent to about 40 percent, or from about 20 percent to about 30 percent of stiffening fiber, specifically reciting all values within these ranges and any ranges created thereby. In one specific example, the fluid management layer 30 may comprise from about 20 percent to about 30 percent by weight stiffening fibers.

Regardless of whether the fluid management layer is utilized in an adult incontinence article or a menstrual article, of critical importance is the ability of the fluid management layer to acquire liquid insults from the topsheet and to pull the liquid far enough from the topsheet, such that the topsheet does not feel wet. To accomplish this, the inventors have found that while absorbent fibers adjacent to the topsheet can help pull liquid from the topsheet, too many absorbent fibers can lead to a wet feeling topsheet. As such, the amount of absorbent fibers in the strata closest to the topsheet is of critical importance. Namely too many absorbent fibers in the first carded nonwoven web 214 and/or second carded nonwoven web 224, can lead to a wet feeling topsheet (assuming the first carded nonwoven 214 and the second carded nonwoven 224 are more proximal to the topsheet than the third carded nonwoven 234).

Additionally, while a higher weight percentage of absorbent fibers may be beneficial for fluid insults that are more viscous, e.g. menstrual fluid, the introduction of a higher weight percentage of absorbent fibers can also negatively impact resiliency and stiffness of the fluid management layer. And, too low of a weight percentage of absorbent fibers can result in a more 'wet feeling' topsheet which can create a negative impression of the product in consumers' minds.

Additionally, the inventors have found that adjacent the topsheet, the fluid management layer may comprise a sufficient void volume to allow for quick fluid acquisition. The tradeoff, as mentioned before, is that this beneficial void volume can also trigger false positives in a vision system that inspects visual signals. Generally, for a given basis weight, larger diameter fibers can provide more void volume between adjacent fibers as compared to their smaller diameter counterparts. As such, the fiber size of the fibers in the strata closes to the topsheet is also of critical importance. Namely, if the diameters of the fibers in the first carded nonwoven 214 and/or the second carded nonwoven 224 are too small, this could detrimentally impact the void volume that is created for rapid fluid acquisition (assuming the first carded nonwoven 214 and the second carded nonwoven 224 are more proximal to the topsheet 20 than the third carded nonwoven 234). This could also lead to a wet feeling topsheet.

There are many potential ways to address the opacity metric which the inventors have linked to the false positives of vision systems. As noted above, larger fibers can create more void volume than smaller fibers. And, smaller fibers can create more opacity than their larger fiber counterparts. However, the positioning of these smaller fibers within the fluid management layer can enhance the performance of the fluid management layer or can negatively impact the performance of the fluid management layer. For example, positioning of the smaller fibers adjacent the topsheet could greatly reduce the void volume of the fluid management layer, depending on the weight percentage within the first stratum and/or second stratum.

With the above in mind, the inventors have carefully selected not only the fibers types in each of the strata in the fluid management layer but have also carefully selected the diameters of the fiber types. The fiber types of the individual strata are discussed in additional detail hereafter. It is worth noting that the discussion below regarding fiber types in the strata of the fluid management layer assumes that the first carded nonwoven web 214 is nearer to the topsheet than the third carded nonwoven web 234.

The first carded nonwoven 214 (or first stratum 214) may comprise absorbing fibers, stiffening fibers, and resilient fibers. To achieve sufficient void volume and to ensure that liquid insults are removed from the topsheet in a timely manner, the first stratum 214 may comprise from about 10 percent to about 50 percent, from about 12 percent to about 40 percent, or from about 15 percent to about 30 percent by weight, specifically reciting all values within these ranges and any ranges created thereby, of absorbent fibers. In one specific example, the first stratum 214 may comprise from about 15 percent to about 25 percent by weight of absorbing fibers.

The first stratum 214 may further comprise from about 20 percent to about 75 percent, from about 30 percent to about 60 percent, from about 40 percent to about 50 percent by weight, specifically including all values within these ranges and any ranges created thereby of resilient fibers. In one specific example, the first stratum 214 may comprise from about 40 percent to about 50 percent by weight of resilient fibers.

The first stratum 214 may further comprise from about 20 percent to about 75 percent, from about 25 percent to about 60 percent, from about 30 percent to about 45 percent by weight, specifically including all values within these ranges and any ranges created thereby of stiffening fibers. In one specific example, the first stratum 214 may comprise from about 30 percent to about 45 percent by weight of stiffening fibers.

The second carded nonwoven 224 (or second stratum 224) may be constructed similar to the first stratum 214 or at least within the ranges specified for the first stratum. Such a construction for the second stratum 224 would facilitate manufacturing to some extent. Recall also that the second stratum 224 is optional. However, as the second stratum 224 is disposed more distal from the topsheet 20 than the first stratum 214, void volume could be adjusted slightly downward. So, smaller diameter fibers may be utilized in the second stratum 224 to help overcome the false positive vision system problem discussed heretofore.

Regarding the third carded nonwoven 234 (or third stratum 234), the configuration of this stratum can vary. Where the third stratum 234 forms a portion of the second surface 300B of the fluid management layer 30, the third stratum 234 may be constructed to reduce the likelihood of false positives associated with visual signal detection in vision systems. Additionally, the third stratum 234 may have sufficient capability to acquire and distribute fluid which is within the void volume of the first stratum 214 and/or second stratum 224. To reduce the likelihood of false positives associated with visual signal detection by vision systems, the inventors have found that smaller diameter fibers may be utilized in the third stratum 234. And, to appropriately deliver the acquisition and distribution attributes desired, absorbent fibers can be utilized. So, the third stratum 234 may comprise from about 50 percent to about 100 percent, from about 60 percent to about 90 percent, or from about 70 percent to about 80 percent by weight, specifically reciting all values within these ranges and any ranges created thereby, of absorbent fibers. In one specific example, the third stratum 234 may comprise 100 percent absorbing fibers.

As mentioned previously, the fluid management layers of the present disclosure can provide their respective absorbent articles with great fluid handling and opacity characteristics. Where caliper, resiliency, and a soft cushiony feel are the objective, the weight percentage of stiffening fibers may be greater than or equal to the weight percentage of resilient fibers. The weight percentage of absorbent fibers can be greater than the weight percentage of resilient fibers and/or stiffening fibers. The latter is particularly true where the fluid management layer of the present disclosure will be utilized in an adult incontinence article. In general, a higher weight percentage of absorbent fibers is considered to be beneficial in rapidly absorbent fluid insults; however, given the proximity of the absorbing fibers to the topsheet, it is beneficial for the absorbent core to dewater the absorbing fibers. Where there is a larger percentage of absorbing fibers, typically a larger core is required to dewater the absorbent fibers. This typically leads to higher costs. With this in mind, a ratio of absorbent fibers in the fluid management layers of the present disclosure to stiffening fibers by weight percentage can be from about 3:1 to about 1.2:1, from about 2.5:1 to about 1.3:1, from about 2:1 to about 1.4:1, specifically reciting all values within these ranges and any ranges created thereby Similarly a ratio of absorbent fibers to resilient fibers by weight percentage can be from about 3:1 to about 1.3:1, from about 2.75:1 to about 1.5:1, or from about 2.5:1 to about 1.6:1, specifically reciting all values within these ranges and any ranges created thereby.

The fluid management layer of the present disclosure may comprise heterogeneous structures. For example, as discussed, fluid management layer of the present disclosure may comprise a larger percentage of cellulose on one side of the fluid management layer versus the opposing side. So, the first surface 300A may comprise a lower percentage of absorbent fibers than the opposing second surface 300B according to the SEM method for Determining Quantity of cellulosic fibers. Fluid management layers of the present disclosure may have a fiber ratio of absorbent fibers on the first side versus the second side or vice versa of from about 5:1 to about 1.5:1; or from about 4.5:1 to about 1.5:1; or from about 4:1 to about 1.5:1.

Regarding the stiffening fibers and resilient fibers in the third stratum 234, as noted the third layer should be provided with the ability to acquire and distribute fluid from the void volume of the first stratum 214 and the second stratum 224. As such, the amount of either stiffening fibers or resilient fibers should be carefully reviewed. As noted previously, neither stiffening and nor resilient fibers are required in the third stratum 234, e.g. 0 weight percent. With this in mind, the third stratum may comprise between 0 percent to about 30 percent, from about 0 percent to about 25 percent, or from about 0 percent to about 20 percent by weight, specifically including all values within these ranges and any ranges created thereby of stiffening and/or resilient fibers.

Still referring to FIGS. 1A-3, where absorbent fibers are utilized, any suitable diameter of absorbing fiber may be utilized. A suitable measure of diameter can be linked to linear density. For the first stratum 214 and/or second stratum 224, larger linear density values may be utilized as increased void volume can be desirable. For example, in the first stratum 214 and/or the second stratum 224 the absorbent fiber linear density may range from about 1 dtex to about 4 dtex, about 1.0 dtex to about 3.7 dtex, or from about 1.0 dtex to about 3.5 dtex, specifically reciting all values within these ranges and any ranges created thereby. In one specific example, the absorbent fiber may comprise a dtex of about 1.7 dtex.

However, for the third stratum 234, the linear density may need to be decreased to help with the visual signal detection. So, the linear density of the absorbent fibers in the third stratum 234 may range from about 1 dtex to about 3 dtex, about 1.4 dtex to about 2.7 dtex, or from about 1.7 dtex to about 2.0 dtex, specifically reciting all values within these ranges and any ranges created thereby. In one specific example, the absorbent fibers in the third stratum 234 may comprise a dtex of about 1.7.

While it is technically possible to have absorbent fibers within the fluid management layer that have varying linear densities, not all carding equipment may be suited to handle such variation between/among strata. To alleviate the possible processing issues, the absorbent fibers of the fluid management layer may comprise the same linear density throughout all the strata.

The absorbent fibers of the fluid management layer may have any suitable shape. Some examples include trilobal, "H," "Y," "X," "T," or round. Further, the absorbing fibers can be solid, hollow or multi-hollow. Other examples of suitable multi-lobed, absorbent fibers for utilization in the carded staple fiber nonwovens detailed herein are disclosed in U.S. Pat. No. 6,333,108 to Wilkes et al, U.S. Pat. No. 5,634,914 to Wilkes et al., and U.S. Pat. No. 5,458,835 to Wilkes et al. The trilobal shape can improve wicking and improve masking. Suitable trilobal rayon is available from Kelheim Fibres and sold under the trade name Galaxy. While each stratum may comprise a different shape of absorbing fiber, much like mentioned above, not all carding equipment may be suited to handle such variation between/among strata. In one specific example, the fluid management layer comprises round absorbent fibers.

Any suitable absorbent fibers may be utilized. Some conventional absorbent fibers include cotton, rayon or regenerated cellulose or combinations thereof. In one example, the fluid management layer 30 may comprise viscose cellulose fibers. The absorbing fibers may comprise staple length fibers. The staple length of the absorbing fibers can be in the range of about 20 mm to about 100 mm, or about 30 mm to about 50 mm or about 35 mm to about 45 mm, specifically reciting all values within these ranges and any ranges created thereby.

As noted previously, in addition to absorbent fibers, fluid management layer may also comprise stiffening fibers. Stiffening fibers may be utilized to help provide structural integrity to the fluid management layer. The stiffening fibers can help increase structural integrity of the fluid management layer in a machine direction and in a cross machine direction which can facilitate web manipulation during processing of the fluid management layer for incorporation into a disposable absorbent article. With that in mind, the constituent material of the stiffening fibers, the weight percentage of the stiffening fibers, and heat of processing should be carefully selected. The heat stiffening process is discussed hereafter.

Any suitable stiffening fiber may be utilized. Some examples of suitable stiffening fibers include bi-component fibers comprising polyethylene and polyethylene terephthalate components or polyethylene terephthalate and co-polyethylene terephthalate components. The components of the bi-component fiber may be arranged in a core sheath arrangement, a side by side arrangement, an eccentric core sheath arrangement, a trilobal arrangement, or the like. In one specific example, the stiffening fibers may comprise bi-component fibers having polyethylene/polyethylene terephthalate components arranged in a concentric, core—sheath arrangement where the polyethylene is the sheath. As another example, monocomponent fibers may be utilized, and the constituent material of the monocomponent may comprise polypropylene or polylactic acid (PLA). It is worth noting that these components, e.g. polypropylene and polylactic acid can also be utilized in bi-component fibers as well.

The stiffening fibers can be polyethylene terephthalate (PET) fibers, or other suitable non-cellulosic fibers known in the art. The staple length of the stiffening fibers can be in the range of about 28 mm to about 100 mm, or in the range of about 37 mm to about 50 mm. Some carded staple fiber nonwovens include stiffening fibers with a staple length of about 38 mm to 42 mm. The PET fibers can have any suitable structure or shape. For example, the PET fibers can be round or have other shapes, such as spiral, scalloped oval, trilobal, scalloped ribbon, and so forth. Further, the PET fibers can be solid, hollow or multi-hollow. In some embodiments of the carded staple fiber nonwoven, the stiffening fibers may be fibers made of hollow/spiral PET. Optionally, the stiffening fibers may be spiral-crimped or flat-crimped. The stiffening fibers may have a crimp value of between about 4 and about 12 crimps per inch (cpi), or between about 4 and about 8 cpi, or between about 5 and about 7 cpi, or between about 9 and about 10 cpi. Particular non-limiting examples of stiffening fibers can be obtained from Wellman, Inc. Ireland under the trade names H1311 and T5974. Other examples of suitable stiffening fibers for utilization in the carded staple fiber nonwovens detailed herein are disclosed in U.S. Pat. No. 7,767,598 to Schneider et al.

Other suitable examples of stiffening fibers include polyester/co-extruded polyester fibers. The stiffening fibers may be so-called bi-component fibers, where individual fibers are provided from different materials, usually a first and a second polymeric material. The two materials may be chemically different (hence the fibers are chemically heterogeneous) or they may differ only in their physical properties while being chemically identical (hence the fibers are chemically homogeneous). For example, may the intrinsic viscosity of the two materials be different, which has been found to influence the crimping behavior of the bi-component fibers. Bi-component fibers that are suitable as stiffening fibers are side-by-side bi-component fibers as disclosed for example in WO 99/00098. The stiffening fibers may also be a blend of bi-component fibers with polyester fibers.

With specific reference to bicomponent fibers comprised of a polypropylene/polyethylene fiber composition, in a cross-sectional view of a fiber, the material with a higher softening temperature can provide the central part (i.e., the core) of the fiber. The core typically is responsible for the bicomponent fiber's ability to transmit forces and have a certain rigidity or otherwise provide structures with resiliency. The outer coating on the core (i.e., the sheath) of the fiber can have a lower melting point and is used to facilitate thermally bonding of substrates comprising such fibers. In one embodiment, a polypropylene core is provided with a polyethylene coating on the outside, such that about 50%, by weight, of the fiber material is polypropylene and 50%, by weight, of the fiber material is polyethylene. Other quantitative amounts can of course be selected. For example, bicomponent fibers can have a composition from about 30% to about 70%, by weight, polyethylene, while others have about 35% to about 65%, by weigh polyethylene. In some embodiments, bicomponent fibers can have a composition from about 40% to about 60% or about 45% to about 55%, by weight, polyethylene.

Another suitable bi-component stiffening fiber is a fiber of circular cross section with a hollow space in the centre that is spiral crimped. It is preferred that 10-15% of the cross sectional area are hollow, or between 20-30% of the cross sectional area are hollow. Without wishing to be bound by theory, it is believed that the spiral crimping of fibers is beneficial for their liquid acquisition and distribution behaviour. It is assumed that the spiral crimp increases the void space in an acquisition member formed by such fibers. Often, an absorbent article, when being worn, is exposed to a certain pressure exerted by the wearer, which potentially decreases the void space in the acquisition member. Having good permeability and sufficient void space available are important for good liquid distribution and transport. It is further believed that the bi-component spiral-crimped fibers as described above are suitable to maintain sufficient void volume even when an acquisition member is exposed to pressure. Also, spiral-crimped fibers believed to provide for good permeability as for a given fiber dtex value, the hollow fiber cross-section allows for a larger outer diameter of the fiber as compared to a compact cross-section. The outer diameter of a fiber appears to determine the permeability behavior of an acquisition member formed by such fibers.

Any suitable size of stiffening fiber may be utilized in the first stratum 214 and/or second stratum 224. Suitable linear densities of stiffening fiber may be from about 1.7 dtex to about 12 dtex, from about 4 dtex to about 10 dtex, or from about 5 dtex to about 7 dtex, specifically reciting all values within these ranges and any ranges created thereby. In one specific example, the stiffening fibers may comprise 5.5 dtex to about 5.8 dtex polyethylene terephthalate/polyethylene fibers for an incontinence article.

Similar to the absorbent fibers in the third stratum 234, stiffening fibers comprised by the third stratum 234 may comprise lower linear densities than those of their first and/or second stratum counterparts. Where the third stratum 234 comprises stiffening fibers, the linear density may range from about 0.9 dtex to about 6 dtex, from about 1.3 dtex to about 3 dtex, or from about 1.6 dtex to about 2.5 dtex, specifically reciting all values within these ranges or any ranges created thereby.

As noted previously, the fluid management layer may be heat treated (heat stiffened). This heat treatment can create connection points amongst the stiffening fibers of the fluid management layer 30. So, where there is a higher percentage of stiffening fibers, more connection points may be created. Too many connection points can yield a much stiffer fluid management layer which may negatively impact comfort. As such, the weight percentage of the stiffening fibers is of critical importance when designing an absorbent article.

With regard to the heat stiffening process, any suitable temperature may be utilized. And, the suitable temperature may be impacted, in part, by the constituent chemistry of the stiffening fibers as well as by the processing fluid management layer web. The fluid management layer web may be heat stiffened at a temperature of 132 degrees Celsius. It is also worth noting, that in order to provide a uniform stiffness property across the fluid management layer, any heating operation should be set up to provide uniform heating to the fluid management layer web. Even small variations in temperature can greatly impact the tensile strength of the fluid management layer.

As noted previously, the fluid management layer of the present disclosure may additionally comprise resilient fibers.

The resilient fibers can help the fluid management layer maintain its permeability. Any suitable size fiber may be utilized. For example, the resilient fibers can have a linear density of about 4 dtex to about 12 dtex, from about 6 dtex to about 11 dtex, or from about 8 dtex to about 10 dtex, specifically reciting all values within these ranges and any ranges created thereby. In one specific example, the resilient fibers may comprise a linear density of from about 6.7 dtex to about 10 dtex hollow spiral polyethylene terephthalate fibers.

It is worth noting, that if smaller fiber sizes are utilized, the resiliency of the fluid management layer would be expected to decrease. And, with the decreased size at the same weight percentage, a higher number of fibers per gram would equate to a decrease in permeability of the fluid management layer.

Similar to the absorbent fibers in the third stratum 234, resilient fibers comprised by the third stratum 234 may comprise lower linear densities than those of their first and/or second stratum counterparts. Where the third stratum 234 comprises resilient fibers, the linear density may range from about 0.9 dtex to about 12 dtex, from about 1.3 dtex to about 9 dtex, or from about 1.6 dtex to about 6 dtex, specifically reciting all values within these ranges or any ranges created thereby.

The resilient fibers can be any suitable thermoplastic fiber, such as polypropylene (PP), polyethylene terephthalate, or other suitable thermoplastic fibers known in the art. The staple length of the resilient fibers can be in the range of about 20 mm to about 100 mm, or about 30 mm to about 50 mm or about 35 mm to about 45 mm. The thermoplastic fibers can have any suitable structure or shape. For example, the thermoplastic fibers can be round or have other shapes, such as spiral, scalloped oval, trilobal, scalloped ribbon, and so forth. Further, the PP fibers can be solid, hollow or multi-hollow. The resilient fibers may be solid and round in shape. Other suitable examples of resilient fibers include polyester/co-extruded polyester fibers. Additionally, other suitable examples of resilient fibers include bi-component fibers such as polyethylene/polypropylene, polyethylene/polyethylene terephthalate, polypropylene/polyethylene terephthalate. These bi-component fibers may be configured as a sheath and a core. The bi-component fibers may provide a cost-effective way to increase basis weight of the material while additionally enabling optimization of the pore size distribution.

It is worth noting that the stiffening fibers and resilient fibers should be carefully selected. For example, while the constituent chemistries of the stiffening fibers and the resilient fibers may be similar, resilient fibers should be selected such that their constituent material's melting temperature is higher than that of the stiffening fibers. Otherwise, during heat treatment, resilient fibers could bond to stiffening fibers and vice versa and could create an overly rigid structure.

Several samples were created and tested to evaluate their opacity and caliper. Opacity was determined to be dispositive regarding whether a particular sample would reduce the likelihood of false positive in a vision system evaluating visual signals. Thirteen different samples were tested for opacity. Each of the samples was a hydroentangled, carded, staple-fiber nonwoven comprising strata.

Sample Description:

Sample 1: 50 gsm spunlace; first, second, and third strata are homogeneous, with each having: 25 percent trilobal rayon, 3.3 dtex; 30 percent polyethylene terephthalate/polyethylene bico, 5.8 dtex; and 45 percent hollow spiral, polyethylene terephthalate fibers, 10 dtex. Sample 1 was described in additional detail in U.S. Patent Application Publication No. US2018/0098893.

Sample 2: 60 gsm spunlace: first, second, and third strata are homogeneous, with each having: 25 percent trilobal rayon, 3.3 dtex; 30 percent polyethylene terephthalate/polyethylene bico, 5.8 dtex; and 45 percent hollow spiral, polyethylene terephthalate fibers, 10 dtex. Sample 2 was described in additional detail in U.S. Patent Application Publication No. US2018/0098893.

Sample 3: 50 gsm spunlace: first and second strata are homogeneous, with each having: 25 percent trilobal rayon, 3.3 dtex; 30 percent polyethylene terephthalate/polyethylene bico, 5.8 dtex; and 45 percent hollow spiral, polyethylene terephthalate fibers, 10 dtex. The third stratum had 100 percent trilobal rayon, 3.3 dtex.

Sample 4: 60 gsm spunlace: first and second strata are homogeneous, with each having: 25 percent trilobal rayon, 3.3 dtex; 30 percent polyethylene terephthalate/polyethylene bico, 5.8 dtex; and 45 percent hollow spiral, polyethylene terephthalate fibers, 10 dtex. The third stratum had 100 percent trilobal rayon, 3.3 dtex.

Sample 5: 50 gsm spunlace: first and second strata are homogeneous, with each having: 25 percent trilobal rayon, 3.3 dtex; 30 percent polyethylene terephthalate/polyethylene bico, 5.8 dtex; and 45 percent hollow spiral, polyethylene terephthalate fibers, 10 dtex. The third stratum had 100 percent round rayon, 1.7 dtex.

Sample 6: 60 gsm spunlace: first and second strata are homogeneous, with each having: 25 percent trilobal rayon, 3.3 dtex; 30 percent polyethylene terephthalate/polyethylene bico, 5.8 dtex; and 45 percent hollow spiral, polyethylene terephthalate fibers, 10 dtex. The third stratum had 100 percent round rayon, 1.7 dtex.

Sample 7: 50 gsm spunlace: first and second strata are homogeneous, with each having: 25 percent trilobal rayon, 3.3 dtex; 30 percent polyethylene terephthalate/polyethylene bico, 4.4 dtex; and 45 percent hollow spiral, polyethylene terephthalate fibers, 10 dtex. The third stratum had 100 percent round rayon, 1.7 dtex.

Sample 8: 60 gsm spunlace: first and second strata are homogeneous, with each having: 25 percent trilobal rayon, 3.3 dtex; 30 percent polyethylene terephthalate/polyethylene bico, 4.4 dtex; and 45 percent hollow spiral, polyethylene terephthalate fibers, 10 dtex. The third stratum had 100 percent round rayon, 1.7 dtex.

Sample 9: 55 gsm spunlace: first and second strata are homogeneous, with each having 25 percent viscose rayon round, 1.7 dtex; 30 percent polyethylene terephthalate/polyethylene bico, 5.8 dtex; and 45 percent hollow spiral, polyethylene terephthalate fibers, 10 dtex. The third stratum had 100 percent round rayon, 1.7 dtex.

Sample 10: 110 gsm spunlace: first and second strata are homogeneous, with each having 20 percent viscose rayon round, 1.7 dtex; 40 percent polyethylene terephthalate/polyethylene bico, 5.8 dtex; and 40 percent hollow spiral, polyethylene terephthalate fibers, 10 dtex. The third stratum had 80 percent viscose rayon, 1.7 dtex and 20 percent polyethylene terephthalate hollow spiral fibers, 10 dtex.

Sample 11: 75 gsm spunlace: first and second strata are homogeneous, with each having 20 percent viscose rayon round, 1.7 dtex; 40 percent polyethylene terephthalate/polyethylene bico, 5.8 dtex; and 40 percent hollow spiral, polyethylene terephthalate fibers, 10 dtex. The third stratum had 80 percent viscose rayon, 1.7 dtex and 20 percent polyethylene terephthalate hollow spiral fibers, 10 dtex.

Sample 12: 45 gsm spunlace: only two strata in this sample. The first stratum has 20 percent viscose rayon round, 1.7 dtex; 40 percent polyethylene terephthalate/polyethylene bico, 5.8 dtex; and 40 percent hollow spiral, polyethylene terephthalate fibers, 10 dtex. The second stratum had 80 percent viscose rayon, 1.7 dtex and 20 percent polyethylene terephthalate hollow spiral fibers, 10 dtex.

Sample 13: 50 gsm spunlace: only two strata in this sample. The first stratum has 20 percent viscose rayon round, 1.7 dtex; 40 percent polyethylene terephthalate/polyethylene bico, 5.8 dtex; and 40 percent hollow spiral, polyethylene terephthalate fibers, 10 dtex. The second stratum had 20 percent viscose rayon round, 1.7 dtex; 20 percent polyethylene terephthalate/polyethylene bico, 5.8 dtex; and 60 percent polypropylene fibers, 1.3 dtex.

In order to reduce the likelihood of false positives associated with the vision system analysis of a visual signal, the inventors have determined that the fluid management layer can have an opacity of at least 48.5 percent. Table 1 shows the opacity data for the above samples.

TABLE 1

| Sample No. | Average Opacity (%) | Standard Deviation |
| --- | --- | --- |
| 1 | 38 | 3.5 |
| 2 | 42.9 | 2.1 |
| 3 | 43.2 | 2.7 |
| 4 | 50.8 | 1.6 |
| 5 | 51 | 4.6 |
| 6 | 54.6 | 2.2 |
| 7 | 51.1 | 5.3 |
| 8 | 53.8 | 4.4 |
| 9 | 57.8 | 1.3 |
| 10 | 67.8 | 2.3 |
| 11 | 55.8 | 2.8 |
| 12 | 42.6 | 2.2 |
| 13 | 54.4 | 4.4 |

Again, the inventors have determined that an opacity of at least 48.5 percent is useful in preventing false positives in a vision system that analyzes visual signals. As shown in Table 1, Samples 4-11 and 13 were able to achieve average opacity values which were greater than 48.5 percent. As shown, samples within the present disclosure can have an opacity percentage of between 48.5 to about 70 percent, or between 50 to about 65 percent, or from about 55 percent to about 60 percent.

In addition to the opacity requirement, the inventors have also found that tensile strength of the web can be an important factor as well. For example, where the tensile strength of the web is less than about 18 Newtons in the MD and/or less than about 5 Newtons in the CD, processing issues may occur. For example, where the web width (in the CD) is less than 80 mm, a tensile strength of greater than 18 N in the MD and/or a tensile strength of greater than 5 N in the CD can facilitate the handling of the web. Where the width of the web is larger, lower MD and/or CD tensile strengths may be sufficient to allow reliable web handling during processing. One of the problems that may be produced by lower MD and/or CD tensile strengths is telescoping of material rolls, i.e. roll cores telescope from the center of the roll outward. This can cause major web handling issues and cause a loss of money and time.

The tensile strength (both MD and CD) of a fluid management layer constructed in accordance with the present disclosure is provided in Table 2. And, the MD and CD tensile strength of a conventional fluid management layer is also provided. Caliper for these samples is also provided. Note that for Table 2, the sample constructed in accordance with the present disclosure is Sample 9. The conventional sample was 75 gsm and comprised three homogeneous strata. Each of the strata comprised 35 percent trilobal viscose rayon, 3.3 dtex; 40 percent polypropylene, 6.7 dtex; and 25 percent hollow spiral polyethylene terephthalate, 10 dtex.

TABLE 2

| Measured Attribute | Sample 9 | | Conventional Sample | |
| --- | --- | --- | --- | --- |
| | Average | Std. Dev. | Average | Std. Dev. |
| MD Tensile Strength (N) | 30.91 | 2.7 | 14.9 | 3.06 |
| CD Tensile Strength (N) | 8.32 | 1.34 | 3.54 | 1.05 |
| Caliper mm | 0.67 | 0.036 | 0.98 | 0.17 |

So, for fluid management layers constructed in accordance with the present disclosure, the MD tensile strength may be between about 19N to about 50N, from about 20N to about 40N, or from about 22N to about 35N, specifically including any values within these ranges or any ranges created thereby. Similarly, the CD tensile strength may be between about 5N to about 15N, from about 6N to about 12 N, or from about 7N to about 10N, specifically including any values within these ranges and any ranges created thereby.

Additionally, the inventors have surprisingly found that when utilized in menstrual articles, the fluid management layers of the present disclosure can reduce the size of the stain on the article and/or can reduce the intensity of the stain on the article. Each these attributes can have a profound impact on the wearer of an article. For example, the more intense a stain, e.g. the brighter the red, the more the perception of the user is that the liquid is closer to the body. Similarly, the larger the stain, the more concerned about capacity of the absorbent article the user becomes.

A number of samples were tested to measure stain size. Stain intensity was observed in photographs taken for the evaluation of the stain size.

Sample 14: 70 gsm spunlace: first and second strata are homogeneous, with each having 20 percent viscose rayon round, 1.7 dtex; 30 percent polyethylene terephthalate/polyethylene bico, 5.8 dtex; and 50 percent polyethylene terephthalate fibers, 6.7 dtex. The third stratum had 80 percent round rayon, 1.7 dtex and 20 percent polyethylene terephthalate, 6.7 dtex.

Sample 15: 55 gsm spunlace: homogeneous blend across three strata, with each having 40 percent viscose rayon, 1.7 dtex; 40 percent polypropylene/polyethylene, 1.7 dtex, and 20 percent polyethylene terephthalate, 4.4 dtex.

Figure 8:
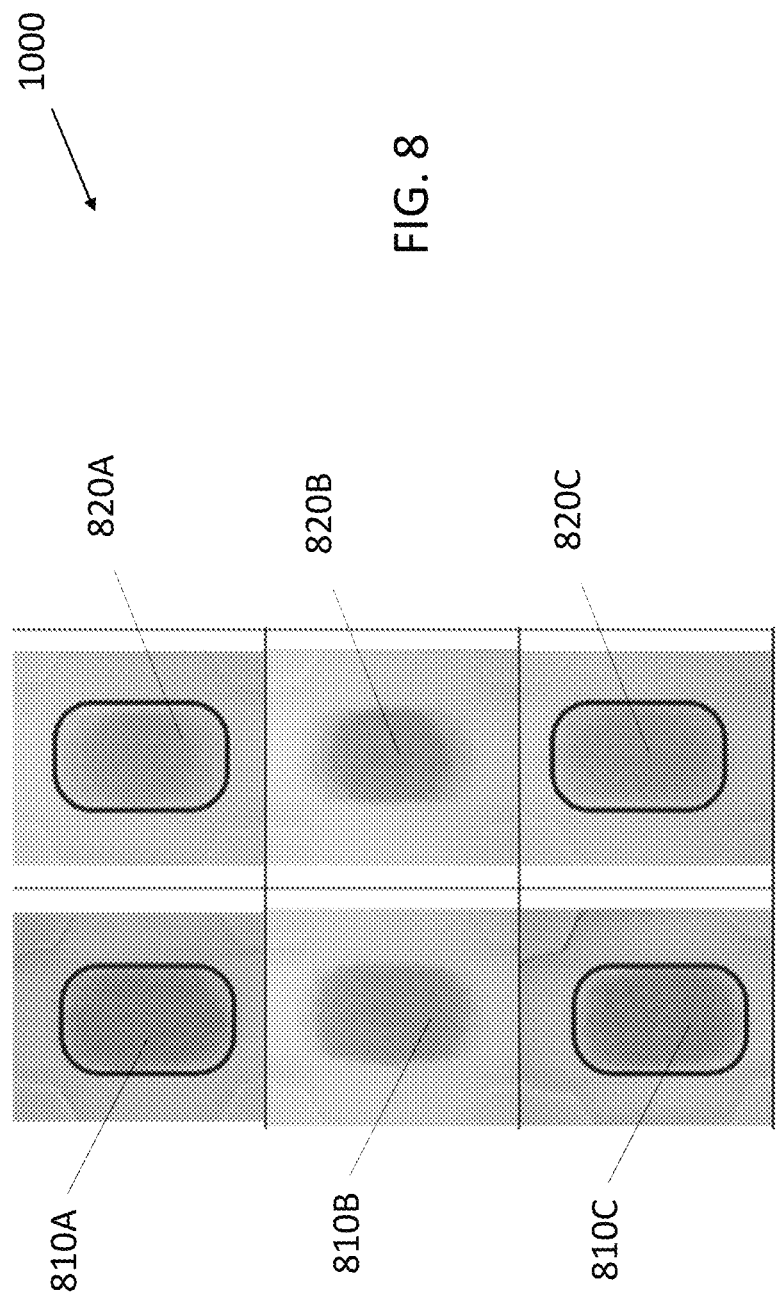
FIG. 8 is a depiction of side by side photographic comparisons of stain sizes of absorbent articles.

FIG. 8 shows a side by side comparison of photographs 1000 of feminine hygiene pads which have had liquid insults applied thereto. The sample feminine hygiene pads 810A, 810B, and 810C comprised the fluid management layer of Sample 15, while the sample feminine hygiene articles 820A, 820B, and 820C comprise the fluid management layer of Sample 14. Each of samples 810A and 820A comprised a film/carded nonwoven laminate topsheet and an airlaid absorbent core having a basis weight of 163 gsm. Each of samples 810B and 820B comprised a film/spunbond nonwoven laminate topsheet and an airlaid absorbent core having a basis weight of 163 gsm. Each of samples 810C and 820C comprised a film topsheet and an airlaid absorbent core having a basis weight of 163 gsm.

As shown, the feminine hygiene pads 820A, 820B, and/or 820C demonstrate a decreased stain size and/or decreased stain intensity. Additional testing at a 15 degree incline had similar results.

Figure 9:
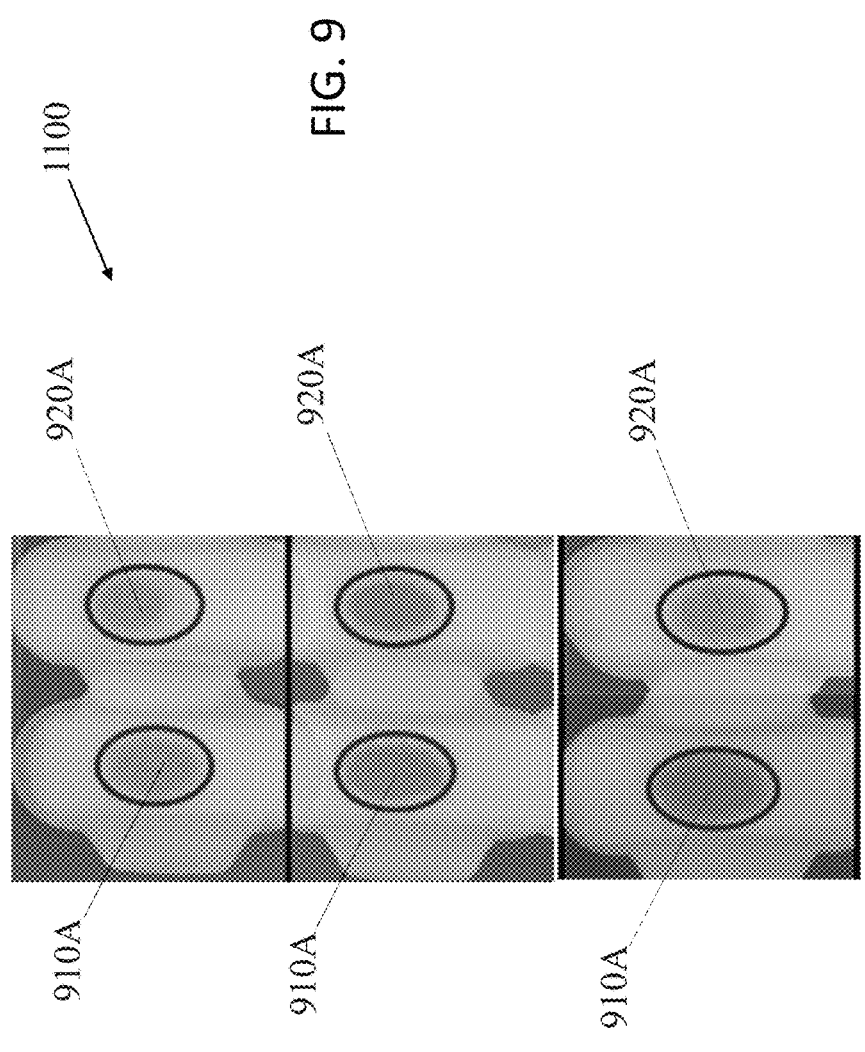
FIG. 9 is a depiction of side by side photograph comparisons of stain sizes of absorbent articles.

FIG. 9 shows a side by side comparison of photographs 1100 of feminine hygiene pads which have had liquid insults applied thereto. The pads were positioned at a 15 degree incline during the liquid insult. The sample feminine hygiene pads 910A, 910B, and 910C comprised the fluid management layer of Sample 15, while the sample feminine hygiene articles 920A, 920B, and 920C comprise the fluid management layer of Sample 14. Each of samples 910A and 920A comprised a film/carded nonwoven laminate topsheet and an airlaid absorbent core having a basis weight of 163 gsm. Each of samples 910B and 920B comprised a film/spunbond nonwoven laminate topsheet and an airlaid absorbent core having a basis weight of 163 gsm. Each of samples 910C and 920C comprised a film/carded nonwoven topsheet and an airlaid absorbent core having a basis weight of 163 gsm. The topsheet for samples 910C and 920C had a greater open area (via apertures) than did the topsheet for samples 910A and 910B, i.e. 8 percent versus 10 percent. An additional sample constructed in accordance with the present disclosure was created by the inventors.

Sample 16: 75 gsm spunlace: first and second strata are homogeneous, with each having 20 percent viscose rayon round, 1.7 dtex; 30 percent polyethylene terephthalate/polyethylene bico, 5.8 dtex; and 50 percent polyethylene terephthalate fibers, 6.7 dtex. The third stratum had 100 percent round viscose rayon, 1.7 dtex.

Samples 14 and 16 have higher basis weights than sample 15. The additional basis weight helps to provide a more lofty and cushiony structure. This can provide a softness benefit to the consumer.

Absorbent Articles

Referring back to FIGS. 1A and 1B, as mentioned previously, disposable absorbent articles of the present disclosure may comprise the topsheet 20 and the backsheet 50. Sandwiched therebetween may be the fluid management layer 30 and the absorbent core 40. Additional layers may be positioned between the topsheet 20 and the backsheet 50.

The topsheet 20 may be joined to the backsheet 50 by attachment methods (not shown) such as those well known in the art. The topsheet 20 and the backsheet 50 may be joined directly to each other in the article periphery and may be indirectly joined together by directly joining them to the absorbent core 40, the fluid management layer 30, and/or additional layers disposed between the topsheet 20 and the backsheet 50. This indirect or direct joining may be accomplished by attachment methods which are well known in the art.

The topsheet 20 may be compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet, while being capable of allowing rapid transfer of fluid through it, may also provide for the transfer or migration of the lotion composition onto an external or internal portion of a wearer's skin.

A suitable topsheet 20 can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof.

Apertured film materials suitable for use as the topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986.

Nonlimiting examples of woven and nonwoven materials suitable for use as the topsheet include fibrous materials made from natural fibers, e.g. cotton, including 100 percent organic cotton, modified natural fibers, synthetic fibers, or combinations thereof. These fibrous materials can be either hydrophilic or hydrophobic, but it is preferable that the topsheet be hydrophobic or rendered hydrophobic. As an option, portions of the topsheet can be rendered hydrophilic, by the use of any known method for making topsheets containing hydrophilic components. Nonwoven fibrous topsheets 20 may be produced by any known procedure for making nonwoven webs, nonlimiting examples of which include spunbonding, carding, wet-laid, air-laid, meltblown, needle-punching, mechanical entangling, thermo-mechanical entangling, and hydroentangling.

The topsheet 20 may be formed from a combination of an apertured film and a nonwoven. For example, a film web and a nonwoven web can be combined as described in U.S. Pat. No. 9,700,463. Alternatively, a film may be extruded onto a nonwoven material which is believed to provided enhanced contact between the film layer and the nonwoven material. Exemplary processes for such a combination are described in U.S. Pat. Nos. 9,849,602 and 9,700,463.

The backsheet 50 may be positioned adjacent a garment-facing surface of the absorbent core 40 and may be joined thereto by attachment methods such as those well known in the art. For example, the backsheet 50 may be secured to the absorbent core 40 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art.

The backsheet 50 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 207 may prevent, or at least inhibit, the exudates absorbed and contained in the absorbent core 205 from wetting articles of clothing which contact the incontinence pad 10 such as undergarments. However, the backsheet 50 may permit vapors to escape from the absorbent core 40 (i.e., is breathable) while in some cases the backsheet 50 may not permit vapors to escape (i.e., non-breathable). Thus, the backsheet 50 may comprise a polymeric film such as thermoplastic films of polyethylene or polypropylene. A suitable material for the backsheet 50 is a thermoplastic film having a thickness of from about 0.012 mm (0.5 mil) to about 0.051 mm (2.0 mils), for example. Any suitable backsheet known in the art may be utilized with the present invention.

The backsheet 50 acts as a barrier to any absorbed bodily fluids that may pass through the absorbent core 40 to the garment surface thereof with a resulting reduction in risk of staining undergarments or other clothing. A preferred material is a soft, smooth, compliant, liquid and vapor pervious material that provides for softness and conformability for comfort, and is low noise producing so that movement does not cause unwanted sound.

Exemplary backsheets are described in U.S. Pat. No. 5,885,265 (Osborn, III.) issued Mar. 23, 1999; U.S. Pat. No. 6,462,251 (Cimini) issued Oct. 8, 2002; U.S. Pat. No. 6,623,464 (Bewick-Sonntag) issued Sep. 23, 2003 or U.S. Pat. No. 6,664,439 (Arndt) issued Dec. 16, 2003. Suitable dual or multi-layer breathable backsheets for use herein include those exemplified in U.S. Pat. Nos. 3,881,489, 4,341,216, 4,713,068, 4,818,600, EP 203 821, EP 710 471, EP 710 472, and EP 793 952.

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness. Suitable single layer breathable backsheets for use herein include those described for example in GB A 2184 389, GB A 2184 390, GB A 2184 391, U.S. Pat. Nos. 4,591,523, 3,989,867, 3,156,242 and WO 97/24097.

The backsheet may be a nonwoven web having a basis weight between about 20 gsm and about 50 gsm. In one embodiment, the backsheet is a relatively hydrophobic 23 gsm spunbonded nonwoven web of 4 denier polypropylene fibers available from Fiberweb Neuberger, under the designation F102301001. The backsheet may be coated with a non-soluble, liquid swellable material as described in U.S. Pat. No. 6,436,508 (Ciammaichella) issued Aug. 20, 2002.

The backsheet has a garment-facing side and an opposite body-facing side. The garment-facing side of the backsheet comprises a non-adhesive area and an adhesive area. The adhesive area may be provided by any conventional means. Pressure sensitive adhesives have been commonly found to work well for this purpose.

The absorbent core 40 of the present disclosure may comprise any suitable shape including but not limited to an oval, a discorectangle, a rectangle, an asymmetric shape, and an hourglass. For example, in some forms of the present invention, the absorbent core 205 may comprise a contoured shape, e.g. narrower in the intermediate region than in the end regions. As yet another example, the absorbent core may comprise a tapered shape having a wider portion in one end region of the pad which tapers to a narrower end region in the other end region of the pad. The absorbent core 40 may comprise varying stiffness in the MD and CD.

The configuration and construction of the absorbent core 40 may vary (e.g., the absorbent core 40 may have varying caliper zones, a hydrophilic gradient, a superabsorbent gradient, or lower average density and lower average basis weight acquisition zones). Further, the size and absorbent capacity of the absorbent core 40 may also be varied to accommodate a variety of wearers. However, the total absorbent capacity of the absorbent core 40 should be compatible with the design loading and the intended use of the disposable absorbent article or incontinence pad 10.

In some forms of the present invention, the absorbent core 40 may comprise a plurality of multi-functional layers that are in addition to the first and second laminates. For example, the absorbent core 40 may comprise a core wrap (not shown) useful for enveloping the first and second laminates and other optional layers. The core wrap may be formed by two nonwoven materials, substrates, laminates, films, or other materials. In a form, the core wrap may only comprise a single material, substrate, laminate, or other material wrapped at least partially around itself.

The absorbent core 40 of the present disclosure may comprise one or more adhesives, for example, to help immobilize the SAP or other absorbent materials within the first and second laminates.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen. These may be used to configure the superabsorbent layers.

Additions to the core of the present disclosure are envisioned. In particular, potential additions to the current multi-laminate absorbent core are described in U.S. Pat. No. 4,610,678, entitled "High-Density Absorbent Structures" issued to Weisman et al., on Sep. 9, 1986; U.S. Pat. No. 4,673,402, entitled "Absorbent Articles With Dual-Layered Cores", issued to Weisman et al., on Jun. 16, 1987; U.S. Pat. No. 4,888,231, entitled "Absorbent Core Having A Dusting Layer", issued to Angstadt on Dec. 19, 1989; and U.S. Pat. No. 4,834,735, entitled "High Density Absorbent Members Having Lower Density and Lower Basis Weight Acquisition Zones", issued to Alemany et al., on May 30, 1989. The absorbent core may further comprise additional layers that mimic the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345. These are useful to the extent they do not negate or conflict with the effects of the below described laminates of the absorbent core of the present invention.

Some examples of a suitable absorbent cores 40 that can be used in the absorbent article of the present disclosure is described in U.S. Patent Application Publication Nos. 2018/0098893 and 2018/0098891.

Figure 4:
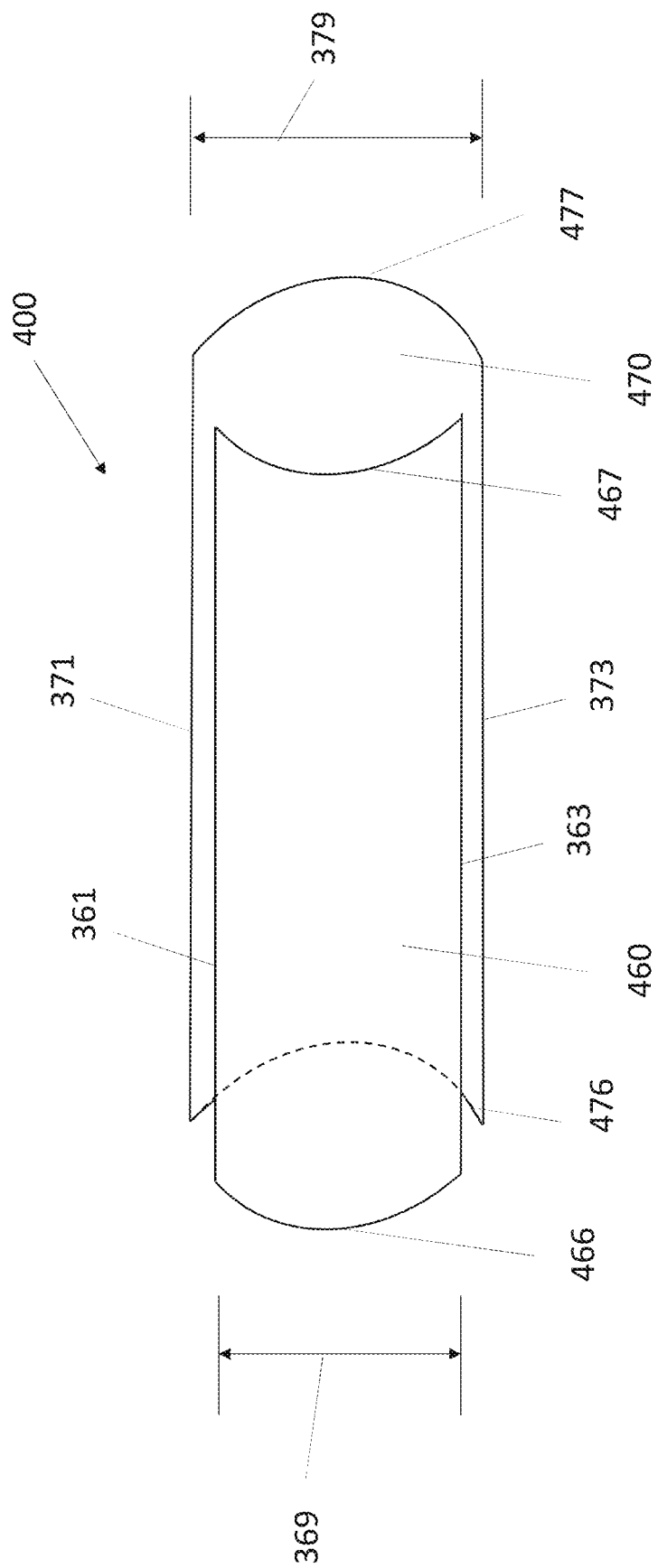
FIG. 4 is a plan view showing an exemplary absorbent system in accordance with the present disclosure.
Figure 5:
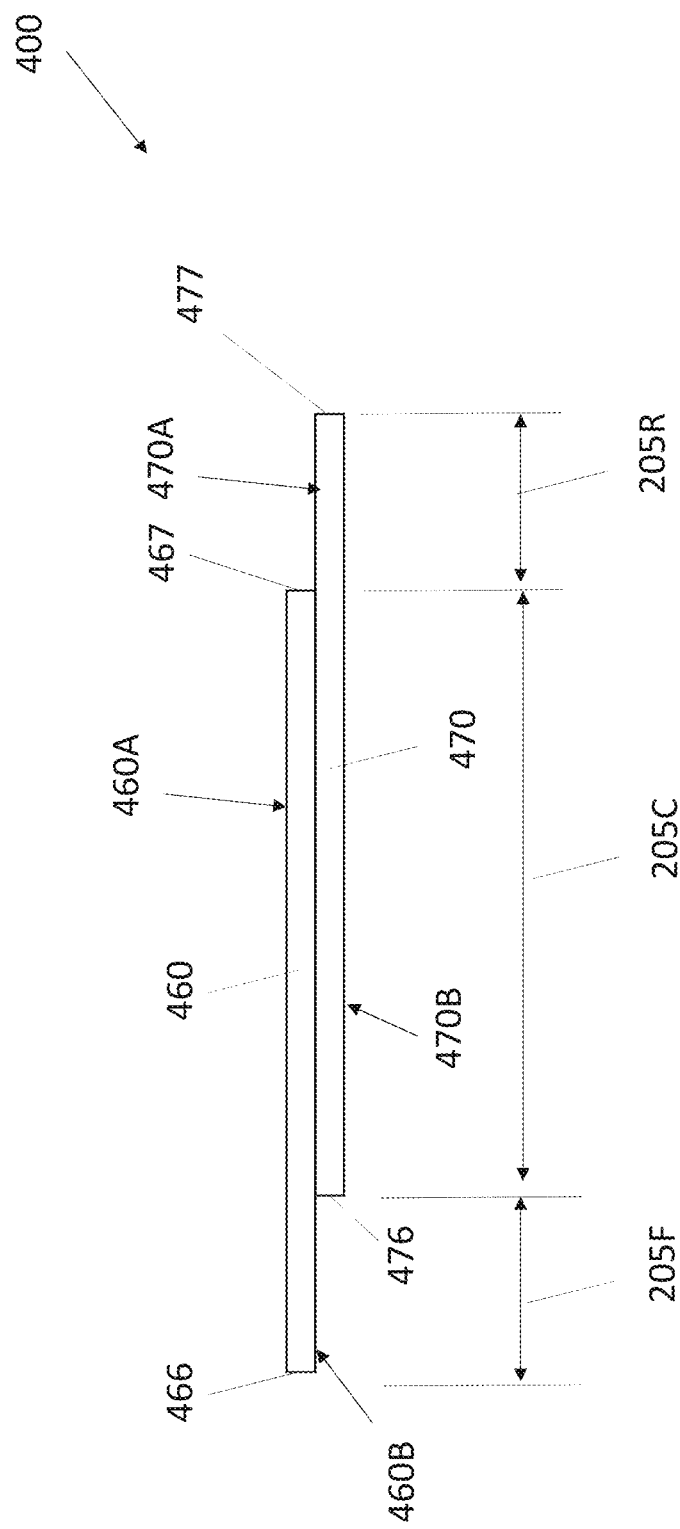
FIG. 5 is an elevation view showing an exemplary absorbent system in accordance with the present disclosure.

Exemplary absorbent core configurations are shown in FIGS. 4-7. FIGS. 4 and 5 depict one exemplary absorbent core configurations which may be utilized in conjunction with the fluid management layer disclosed herein. As shown, a plan view of the pad 10 with the primary topsheet 20 and backsheet 50 have been removed for facilitated viewing of the absorbent core 40. FIG. 5 shows an elevation view of this absorbent system 205 in more detail. For the forms shown in FIGS. 4-7, the absorbent core 40 may comprise multiple layers or multiple absorbent cores. To minimize confusion, the absorbent core 40 in FIGS. 4-7 will be referred to as an absorbent system 400.

Still referring to FIGS. 4 and 5, the absorbent system 400 may comprise a first absorbent core 460 and a second absorbent core 470. As shown, the first absorbent core 460 has a first leading edge 466 and a first trailing edge 467 which opposes the first leading edge 466. Similarly, the second absorbent core 470 comprises a second leading edge 476 and a second trailing edge 477 opposite the second leading edge 476.

The first absorbent core 460 additionally comprises a first edge 361 and a second edge 363. Similarly, the second absorbent core 470 comprises a third edge 371 and a fourth edge 373. As shown, the first absorbent core 460 has a first width 369 and the second absorbent core 470 comprises a second width 379. As shown, the first width 369 may be greater than the second width 379. The respective widths of the first absorbent core 460 and the second absorbent core 470 are discussed hereafter.

Referring now to FIG. 5, the first absorbent core 460 has an upper surface 460A and a lower surface 460B which opposes the upper surface. Similarly, the second absorbent core 470 has an upper surface 470A and a lower surface 470B. Additionally, the first absorbent core 460 and/or the second absorbent core 470 may comprise a laminate structure which includes a plurality of layers, a single layer or a combination of layers. For example, the first absorbent core 460 may comprise a laminate structure while the second absorbent core 470 comprises a single layer or vice versa. Such forms are discussed in additional detail hereafter.

As shown, the first absorbent core 460 may be joined to the second absorbent core 470 in an offset manner or configuration along the length of the absorbent system 400. As used herein "offset" or "offset manner" means that the layers of interest are staggered and that their respective leading edges or trailing edges are not aligned in a z-direction (i.e., the leading edge of one layer or laminate structure is not coterminous with the trailing edge or leading edge of an adjacent underlying or overlying layer or laminate structure) when the layers or laminate structures overlay one another. This offset joinder of the first and second absorbent cores 460 and 470 results in an overlapping and joined area of the two layers that forms a central portion 205C of the absorbent system 400. The central portion 205C of the absorbent core 40 is consequently bounded on each side by a front end portion 205F and a rear end portion 205R, both of the absorbent system 400. In other words, the front end portion 205F and the rear end 205R portion are respectively disposed at opposing ends of the absorbent system 400. As shown in some forms, a distance between the first leading edge 466 and the second leading edge 476 can define a length of the front end portion 205F. Similarly a distance between the second trailing edge 477 and the first trailing edge 467 can define a length of the rear end portion 205R. The second leading edge 476 may be the leading edge of the absorbent core 40 while the first trailing edge 467 may be the trailing edge of the absorbent system 400.

Figure 6:
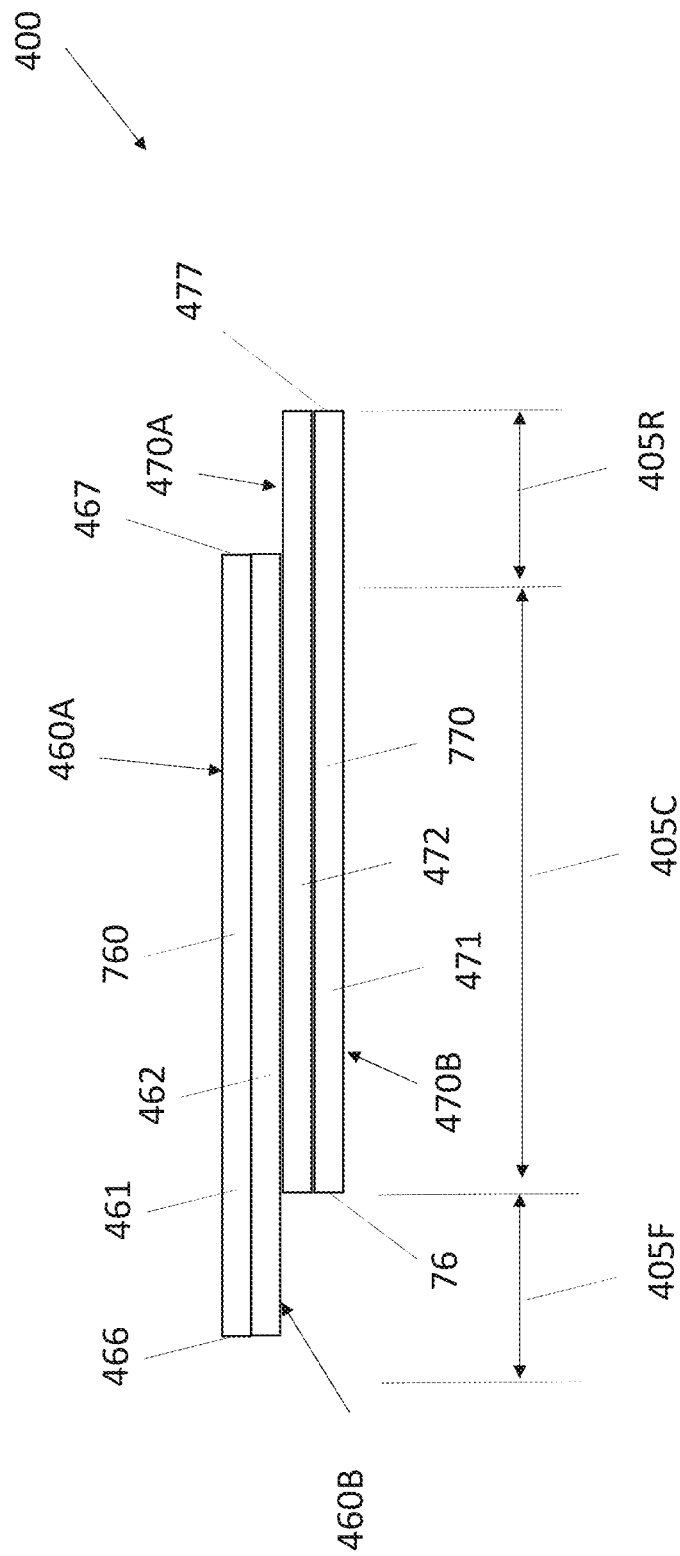
FIG. 6 is an elevation view showing another exemplary absorbent system in accordance with the present disclosure.

As mentioned previously, the first absorbent core 460 and/or the second absorbent core 470 may comprise a plurality of webs and/or layers themselves. Referring now to FIGS. 4-6, for example, the first absorbent core 460 may comprise a first superabsorbent layer 461 disposed on a first distribution layer 462, i.e. a first absorbent core laminate 760. And, the second absorbent core 470 may comprise a second superabsorbent layer 471 disposed on a second distribution layer 472, i.e. a second absorbent core laminate 770. In some forms, the first distribution layer 462 is joined to the second distribution layer 472 in an offset manner or configuration along the length of the core. This offset joinder of the first and second distribution layers 462, 472 results in an overlapping and joined area of the two laminates that forms a central portion 405C of the absorbent system 400. The central portion 405C of the absorbent system 400 is consequently bounded on each side by a front end portion 405F and a rear end portion 405R, both of the core. In other words, the front end portion 405F and the rear end 405R portion are respectively disposed at opposing ends of the absorbent system 400. As shown, the front end portion 405F is formed from the first leading edge 466 of the first absorbent core laminate 760 while the rear end portion 405R of the core 205 is formed by the second trailing edge 77 of the second absorbent core laminate 770.

The first leading edge 466 and second trailing edge 477 of the first and second absorbent core laminates, respectively, oppose each other and form the front end portion 405F and the rear end portion 405R of the absorbent system 400, respectively or vice versa. In other forms, the first trailing edge 467 and second leading edge 476 of the first and second absorbent core laminates may oppose each other and form a front end portion 405F and a rear end portion 405R of the absorbent system 205, respectively or vice versa. In both instances, the first leading edge 466 and second trailing edge 477 may be in the form of a male connection derived from a nested cut of the first and second absorbent cores. Similarly, the first trailing edge 467 and second leading edge 476 may be in the form of a female connection derived from a nested cut of the first and second laminates, respectively.

In an alternate form, the first absorbent core laminate 760 may be joined to superabsorbent layer 471 instead of the second distribution layer 472. In such forms, the laminates may be joined to one another in an offset manner as well except the first distribution layer 462 is joined to the second superabsorbent layer 471 instead of the second distribution layer 472.

In some forms, the overlapping area or region that forms the central portion 205C of the core 205 has at least one characteristic of a greater capacity, a greater void volume, or a greater thickness than the front end portion 205F and the rear end portion 205F of the absorbent system 205. These forms may be particularly useful for providing for heightened leakage protection in the central portion where female users of such pads would typically contact the pad and release fluids.

Referring back to FIGS. 4 and 5, as noted previously, the first absorbent core 460 and/or the second absorbent core 470 may comprise laminate structures. However, in some forms, the first absorbent core 460 and second absorbent core layer 470 may comprise airlaid structures. However, the utilization of airlaid structures may obviate the need for separate distribution layers and superabsorbent layers. In other examples, at least one of the first absorbent core layer 460 or second absorbent core layer 470 may comprise a laminate structure as described above with regard to FIG. 7 while the other of the first absorbent core layer 60 or second absorbent core layer 70 comprise an airlaid structure. Suitable airlaid absorbent core structures are disclosed in U.S. Pat. Nos. 8,105,301 and 8,603,622 and U.S. Patent Application Publication No. 2017/0348166.

Referring now to FIGS. 5 and 6, the first and second superabsorbent layers 461, 471 of the first and second absorbent cores 460, 470 comprise superabsorbent polymers or absorbent gelling materials (AGM). The superabsorbent layer 461 and/or 471 may comprise a carrier web and composition. In such forms, superabsorbent may be deposited on the carrier web to form the superabsorbent layers. The superabsorbent layers may comprise AGM particles or AGM fibers. In general, such AGM's have been used only for their fluid-absorbing properties. Such materials form hydrogels on contact with liquid (e.g., with urine, blood, and the like). One highly preferred type of hydrogel-forming, absorbent gelling material is based on the hydrolyzed polyacids, especially neutralized polyacrylic acid. These preferred superabsorbent polymers will generally comprise substantially water-insoluble, slightly cross-linked, partially neutralized, hydrogel-forming polymer materials prepared from polymerizable, unsaturated, acid-containing monomers.

The superabsorbent layer 461 and/or 471 or portions thereof of the present disclosure may be substantially free of airfelt and are thus distinct from mixed layers that may include airfelt. As used herein, "substantially free of airfelt" means less than 5%, 3%, 1%, or even 0.5% of airfelt. In some forms, there may be no measurable airfelt in the superabsorbent layers. In the case of the first superabsorbent layer, it is preferably disposed onto the first distribution layer discontinuously. And as noted previously, the second superabsorbent layer may, in conjunction with the first superabsorbent layer or independently thereof, be disposed on the second distribution layer discontinuously. As used herein "discontinuously" or "in a discontinuous pattern" means that the superabsorbent polymers are applied onto the first distribution layer in a pattern of disconnected shaped areas. These areas of superabsorbent polymers or areas free of superabsorbent polymer may include, but are not limited to linear strips, non-linear strips, circles, rectangles, triangles, waves, mesh, and combinations thereof. The first superabsorbent layer like the second superabsorbent layer may, however, be disposed onto its respective distribution layer in a continuous pattern. As used herein "continuous pattern" or "continuously" means that the material is deposited and or secured to a superabsorbent carrier material and/or the adjacent distribution layer in an uninterrupted manner such that there is rather full coverage of the distribution layer by the superabsorbent polymer.

The first and second superabsorbent layers may comprise superabsorbent polymers that are the same. In other embodiments, the first and second superabsorbent layers may comprise superabsorbent polymers that are different from one another. This is may be in addition to the different deposition patterns that are discussed above.

The superabsorbent layers are disposed having a thickness of 0.2 mm, 0.3 mm, 0.4 mm, or 0.5 mm to 1 mm, 1.2 mm, 1.4 mm, 1.8 mm, or 2 mm. The first and second superabsorbent layers may have the same or different cross-direction widths as applied to their respective distribution layers. For instance, the cross-direction widths of the first and second superabsorbent layers may be from 20 mm, 25 mm, 30 mm, 35 mm, or 40 mm to 50 mm, 60 mm, 65 mm, 70 mm, 80 mm, or 90 mm. Alternatively, in embodiments where the widths of the first and second superabsorbent layers differ from one another in the cross-direction width, the first superabsorbent layer may have a lesser cross-direction width than the second superabsorbent layer. In particular, the first superabsorbent layer may have a cross-direction width that is less than about 95%, 90%, 80%, 70%, or even 60% of the width of the second superabsorbent layer.

In certain embodiments, the one or both of the first and second superabsorbent layers span greater than greater than about 50%, 60%, 70%, 80%, 90%, or even 95% of the cross-direction width of a superabsorbent carrier layer and/or the respective adjoining first or second distribution layer.

Like the optional layers that may be included in the chassis, the absorbent system may also comprise similar optional layers. The following descriptions and attributes of the optional layers are also suitable for use in the carrier web. For the sake of facility, the term "webs" shall encompass the optional layer web as well as carrier webs. The optional layers and/or carrier webs may be webs selected from the group consisting of a fibrous structure, an airlaid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof.

These optional layers and/or carrier webs may comprise materials such as creped cellulose wadding, fluffed cellulose fibers, airfelt, and textile fibers. The materials of the webs may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The optional layers may be any combination of the materials listed above and/or a plurality of the materials listed above, alone or in combination.

The materials of the webs may be hydrophobic or hydrophilic depending on their placement within the chassis. The materials of these optional layer/webs may comprise constituent fibers comprising polymers such as polyethylene, polypropylene, polyester, and blends thereof. The fibers may be spunbound fibers. The fibers may be meltblown fibers. The fibers may comprise cellulose, rayon, cotton, or other natural materials or blends of polymer and natural materials. The fibers may also comprise a superabsorbent material such as polyacrylate or any combination of suitable materials. The fibers may be monocomponent, bicomponent, and/or biconstituent, non-round (e.g., capillary channel fibers), and may have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e., capillary and round) and the like. The constituent fibers may range from about 0.1 denier to about 100 denier.

The webs may include thermoplastic particulates or fibers. The materials, and in particular thermoplastic fibers, may be made from a variety of thermoplastic polymers including polyolefins such as polyethylene (e.g., PULPEX™) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber may be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse™ by Glyco Chemical, Inc. of Greenwich, Conn. Besides nonionic surfactants, anionic surfactants may also be used. These surfactants may be applied to the thermoplastic fibers at levels of, for example, from about 0.2 to about 1 g/cm$^2$ of thermoplastic fiber.

Suitable thermoplastic fibers may be made from a single polymer (monocomponent fibers), or may be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the webs of this disclosure may include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON™, CELBOND™, or CHISSO™ bicomponent fibers). These bicomponent fibers may be concentric or eccentric. As used herein, the terms "concentric" and "eccentric" refer to whether the sheath has a thickness that is even, or uneven, through the cross-sectional area of the bicomponent fiber. Eccentric bicomponent fibers may be desirable in providing more compressive strength at lower fiber thicknesses. Suitable bicomponent fibers for use herein may be either uncrimped (i.e., unbent) or crimped (i.e., bent). Bicomponent fibers may be crimped by typical textile means such as, for example, a stuffer box method or the gear crimp method to achieve a predominantly two-dimensional or "flat" crimp.

The length of bicomponent fibers may vary depending upon the particular properties desired for the fibers and the web formation process. Typically, in an airlaid web, these thermoplastic fibers have a length from about 2 mm to about 12 mm long such as, for example, from about 2.5 mm to about 7.5 mm long, and from about 3.0 mm to about 6.0 mm long. Nonwoven fibers may be between 5 mm long and 75 mm long, such as, for example, 10 mm long, 15 mm long, 20 mm long, 25 mm long, 30 mm long, 35 mm long, 40 mm long, 45 mm long, 50 mm long, 55 mm long, 60 mm long, 65 mm long, or 70 mm long. The properties-of these thermoplastic fibers may also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine may have a decitex in the range from about 1.0 to about 20 such as, for example, from about 1.4 to about 10, and from about 1.7 to about 7 decitex.

The compressive modulus of these thermoplastic materials, and especially that of the thermoplastic fibers, may also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers may be used to alter the properties, and especially the density characteristics, of the respective thermally bonded fibrous matrix.

The webs may also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON™, and KODEL™), high melting crimped polyester fibers (e.g., KODEL™ 431 made by Eastman Chemical Co.) hydrophilic nylon (HYDROFIL™), and the like. Suitable fibers may also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length may vary depending upon the particular properties desired for these fibers. Typically they have a length from about 0.3 to 7.5 cm, such as, for example from about 0.9 to about 1.5 cm. Suitable nonbonding thermoplastic fibers may have a decitex in the range of about 1.5 to about 35 decitex, such as, for example, from about 14 to about 20 decitex.

The first and second distribution layers are useful for wicking bodily fluids away from the skin of a wearer to facilitate comfort of continued wear after a release. In some forms, the support web may comprise the distribution layer. In some forms, the support web may be configured similar to the carrier web described herein. In some forms, the first and second distribution layers of the first and/or second laminates not only face one another but are joined in an offset manner to form part of the core. The distribution layers comprise one or more of cellulose and commuted wood pulp. This may be in the form of airlaid. The airlaid may be chemically or thermally bonded. In particular, the airlaid may be multi bonded airlaid (MBAL). In this instance, the distribution layer may further comprise a fibrous thermoplastic adhesive material at least partially bonding the airlaid to itself and adjacent distribution layers, superabsorbent layers, or other additional (optional) layers. It should be noted that the same materials that are suitable for the optional layers of the chassis are envisioned as suitable for use in the distribution layers. The basis weight for each of the first and second distribution layers range from 80 gsm, 80 gsm, 100 gsm, 110 gsm, 120 gsm, or 130 gsm to 140 gsm, 150 gsm, 160 gsm, 180 gsm, 200 gsm, 220 gsm, or 240 gsm. A preferred basis weight is 135 gsm for each of the distribution layers of the first and second laminates.

Figure 7:
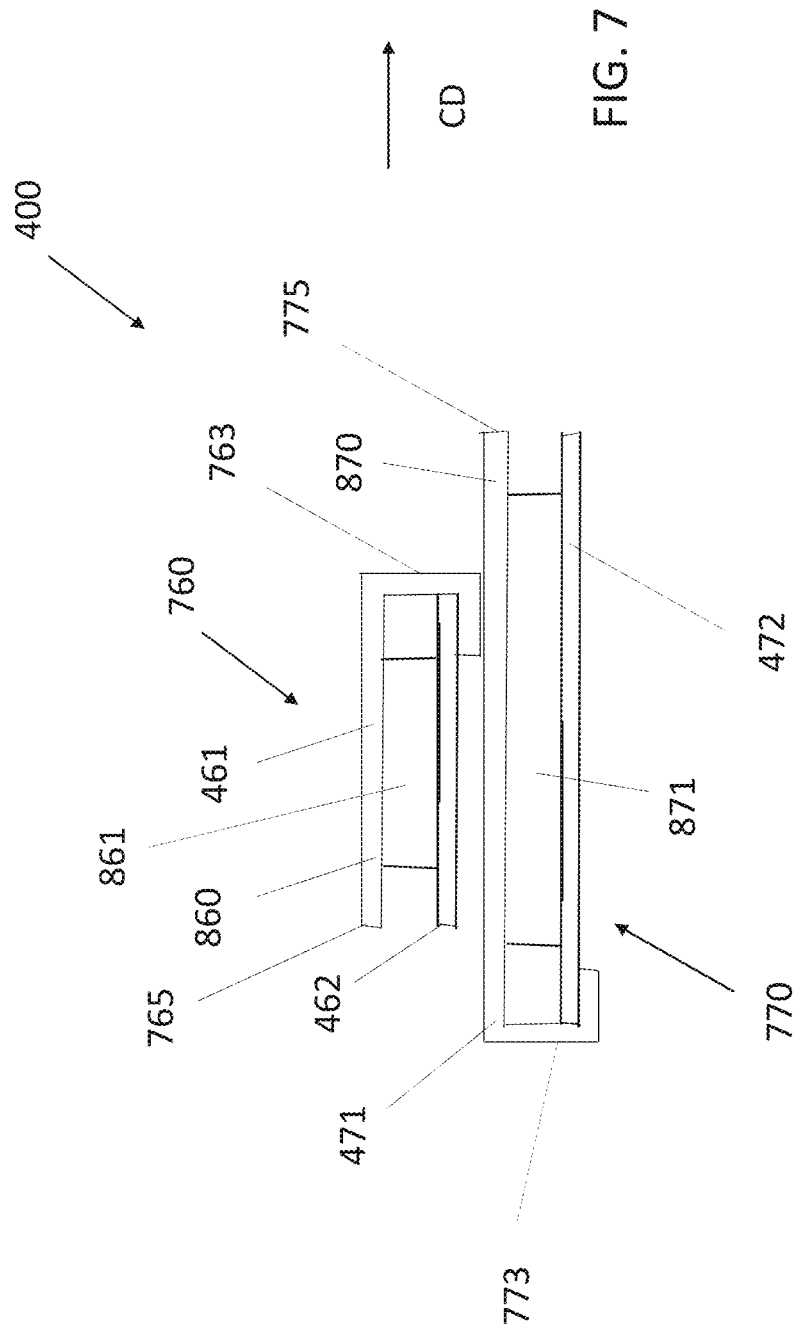
FIG. 7 is a schematic representation showing a cross sectional view of an absorbent system in accordance with the present disclosure.

Referring now to FIGS. 6 and 7, as shown, the absorbent system 400 may be configured such that the first absorbent core laminate 760 comprises the first superabsorbent layer 461 and the first distribution layer 462. The superabsorbent layer 461 may comprise a carrier layer 860 and absorbent material 861 deposited thereon. As shown, the carrier layer 860 may comprise a first side 765 and a folded side 763. As shown, the carrier layer 860 may be folded around the first distribution layer 462 forming an L-wrap at the folded side 763. A portion of the carrier layer 860 may be disposed between the first distribution layer 462 and the second absorbent core laminate 770.

The second absorbent laminate 770 may be similarly configured. For example, the second absorbent laminate 770 may comprise the second superabsorbent layer 471 and the second distribution layer 472. The second superabsorbent layer 471 may comprise a carrier layer 870 and absorbent material 871 disposed thereon. As shown, the carrier layer 870 may comprise a second side 775 and an opposing second folded side 773. The carrier layer 870 may be folded around the second distribution layer 472 forming an L-wrap at folded side 773. A portion of the carrier layer 870 may be disposed between the subjacent to the second distribution layer 472.

There are several other configurations of the absorbent system 400 which may also be utilized. For example, the first folded side 763 may be disposed on the same side of the absorbent system 400 as the second folded side 773. In such configurations, the second distribution layer 472 may be joined to the first distribution layer 462, or the first superabsorbent layer 461 may be joined to the second superabsorbent layer 471. In another configuration, the first superabsorbent layer 461 may be joined to the second distribution layer 472.

The fluid management layer can serve a multitude of functions with absorbent articles of the present disclosure. For example, the fluid management layer described herein may be utilized as a secondary topsheet which is disposed between the topsheet and the absorbent system. The fluid management layer described herein may be utilized as a carrier layer for the superabsorbent layers described herein. Or the fluid management layer of the present disclosure may be utilized in a combination of the above functions, e.g. secondary topsheet and carrier layer.

Additionally, configurations are contemplated where the absorbent system comprises only one absorbent core. The absorbent core for such configurations may comprise a superabsorbent layer and a distribution layer as described herein. And, in such configurations, the carrier layer may be folded on one or both sides of the distribution layer thereby forming a C-wrap around the distribution layer. Portions of the carrier layer may be disposed on an underside of the distribution layer.

The absorbent article 10 may further comprise barrier cuffs. Some examples of other suitable barrier cuffs are described in U.S. Pat. Nos. 4,695,278; 4,704,115; 4,795,454; 4,909,803; U.S. Patent Application Publication No. 2009/0312730. Additional suitable barrier cuffs are described in U.S. Patent Application Publication Nos. 2018/0098893 and 2018/0098891.

Test Methods
Basis Weight

The basis weight of a test sample is the mass (in grams) per unit area (in square meters) of a single layer of material and is measured in accordance with compendial method WSP 130.1. The mass of the test sample is cut to a known area, and the mass of the sample is determined using an analytical balance accurate to 0.0001 grams. All measurements are performed in a laboratory maintained at 23° C.±2° C. and 50%±2% relative humidity and test samples are conditioned in this environment for at least 2 hours prior to testing.

Measurements are made on test samples taken from rolls or sheets of the raw material, or test samples obtained from a material layer removed from an absorbent article. When excising the material layer from an absorbent article, use care to not impart any contamination or distortion to the layer during the process. The excised layer should be free from residual adhesive. To ensure that all adhesive is removed, soak the layer in a suitable solvent that will dissolve the adhesive without adversely affecting the material itself. One such solvent is THF (tetrahydrofuran, CAS 109-99-9, for general use, available from any convenient source). After the solvent soak, the material layer is allowed to thoroughly air dry in such a way that prevents undue stretching or other deformation of the material. After the material has dried, a test specimen is obtained. The test specimen must be as large as possible so that any inherent material variability is accounted for.

Measure the dimensions of the single layer test specimen using a calibrated steel metal ruler traceable to NIST, or equivalent. Calculate the Area of the test specimen and record to the nearest 0.0001 square meter. Use an analytical balance to obtain the Mass of the test specimen and record to the nearest 0.0001 gram. Calculate Basis Weight by dividing Mass (in grams) by Area (in square meters) and record to the nearest 0.01 grams per square meter (gsm). In like fashion, repeat for a total of ten replicate test specimens. Calculate the arithmetic mean for Basis Weight and report to the nearest 0.01 grams/square meter.

Material Compositional Analysis

The quantitative chemical composition of a test specimen comprising a mixture of fiber types is determined using ISO 1833-1. All measurements are performed in a laboratory maintained at 23° C.±2° C. and 50%±2% relative humidity.

Analysis is performed on test samples taken from rolls or sheets of the raw material, or test samples obtained from a material layer removed from an absorbent article. When excising the material layer from an absorbent article, use care to not impart any contamination or distortion to the layer during the process. The excised layer should be free from residual adhesive. To ensure that all adhesive is removed, soak the layer in a suitable solvent that will dissolve the adhesive without adversely affecting the material itself. One such solvent is THF (tetrahydrofuran, CAS 109-99-9, for general use, available from any convenient source). After the solvent soak, the material layer is allowed to thoroughly air dry in such a way that prevents undue stretching or other deformation of the material. After the material has dried, a test specimen is obtained and tested as per ISO 1833-1 to quantitatively determine its chemical composition.

Fiber Decitex (Dtex)

Textile webs (e.g. woven, nonwoven, airlaid) are comprised of individual fibers of material. Fibers are measured in terms of linear mass density reported in units of decitex. The decitex value is the mass in grams of a fiber present in 10,000 meters of that fiber. The decitex value of the fibers within a web of material is often reported by manufacturers as part of a specification. If the decitex value of the fiber is not known, it can be calculated by measuring the cross-sectional area of the fiber via a suitable microscopy technique such as scanning electron microscopy (SEM), determining the composition of the fiber with suitable techniques such as FT-IR (Fourier Transform Infrared) spectroscopy and/or DSC (Dynamic Scanning calorimetry), and then using a literature value for density of the composition to calculate the mass in grams of the fiber present in 10,000 meters of the fiber. All testing is performed in a room maintained at a temperature of 23° C.±2.0° C. and a relative humidity of 50%±2% and samples are conditioned under the same environmental conditions for at least 2 hours prior to testing.

If necessary, a representative sample of web material of interest can be excised from an absorbent article. In this case, the web material is removed so as not to stretch, distort, or contaminate the sample.

SEM images are obtained and analyzed as follows to determine the cross-sectional area of a fiber. To analyze the cross section of a sample of web material, a test specimen is prepared as follows. Cut a specimen from the web that is about 1.5 cm (height) by 2.5 cm (length) and free from folds or wrinkles. Submerge the specimen in liquid nitrogen and fracture an edge along the specimen's length with a razor blade (VWR Single Edge Industrial Razor blade No. 9, surgical carbon steel). Sputter coat the specimen with gold and then adhere it to an SEM mount using double-sided conductive tape (Cu, 3M available from electron microscopy sciences). The specimen is oriented such that the cross section is as perpendicular as possible to the detector to minimize any oblique distortion in the measured cross sections. An SEM image is obtained at a resolution sufficient to clearly elucidate the cross sections of the fibers present in the specimen. Fiber cross sections may vary in shape, and some fibers may consist of a plurality of individual filaments. Regardless, the area of each of the fiber cross sections is determined (for example, using diameters for round fibers, major and minor axes for elliptical fibers, and image analysis for more complicated shapes). If fiber cross sections indicate inhomogeneous cross-sectional composition, the area of each recognizable component is recorded and dtex contributions are calculated for each component and subsequently summed. For example, if the fiber is bi-component, the cross-sectional area is measured separately for the core and sheath, and dtex contribution from core and sheath are each calculated and summed. If the fiber is hollow, the cross-sectional area excludes the inner portion of the fiber comprised of air, which does not appreciably contribute to fiber dtex. Altogether, at least 100 such measurements of cross-sectional area are made for each fiber type present in the specimen, and the arithmetic mean of the cross-sectional area $a_k$ for each are recorded in units of micrometers squared ($m^2$) to the nearest 0.1 μm$^2$.

Fiber composition is determined using common characterization techniques such as FTIR spectroscopy. For more complicated fiber compositions (such as polypropylene core/polyethylene sheath bi-component fibers), a combination of common techniques (e.g. FTIR spectroscopy and DSC) may be required to fully characterize the fiber composition. Repeat this process for each fiber type present in the web material.

The decitex $d_k$ value for each fiber type in the web material is calculated as follows:

$$d_k = 10000 \text{ m} \times a_k \times \rho_k \times 10^{-6}$$

where $d_k$ is in units of grams (per calculated 10,000 meter length), $a_k$ is in units of μm$^2$, and $\rho_k$ is in units of grams per cubic centimeter (g/cm$^3$). Decitex is reported to the nearest 0.1 g (per calculated 10,000 meter length) along with the fiber type (e.g. PP, PET, cellulose, PP/PET bico).

SEM Method to Determine Quantity of Cellulosic Fibers

A Scanning Electron Microscope (SEM) is used to obtain images of both the first side and second side of a material test sample. From these images, the quantity of the cellulosic filaments on each side of the test sample is determined using image analysis. All testing is performed in a room maintained at a temperature of 23° C.±2.0° C. and a relative humidity of 50%±2% and samples are conditioned under the same environmental conditions for at least 2 hours prior to testing.

Obtain a test sample by removing it from an absorbent article, if necessary. When excising the sample from an absorbent article, use care to not impart any contamination or distortion to the sample layer during the process. The test sample is obtained from an area free of folds or wrinkles. A total of 6 replicate test samples are obtained. The test region on each test sample is marked in such a way that will allow for the same area to be analyzed on each side. One suitable way to mark the sidedness of the test region is to use an asymmetrical notch.

Secondary Electron (SE) images are obtained using an SEM such as the FEI Quanta 450 (available from FEI Company, Hillsboro, Oreg.), or equivalent. The instrument is calibrated according to the manufacturer's instructions prior to use to ensure an accurate distance scale. The test region on the first side of the test sample is viewed at a low magnification (e.g. 200×; horizontal field width about 1 mm) such that a representative number of the cellulosic based filaments are clearly visualized for counting purposes, and an image is acquired. At the same test region, images of the second side of the test sample are acquired using the same low magnification used for the first side.

Figure 10:
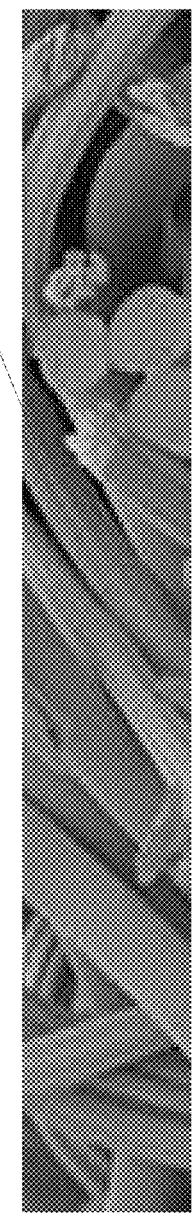
FIG. 10 is an SEM image showing synthetic and viscose fibers.

The low magnification image of the first side of the test sample is opened on a computer running image analysis software, such as Image Pro Plus (available from Media Cybernetics, Rockville, Md.), or equivalent. All of the filaments having a crenulated outer surface (e.g. viscose fibers) within the image are manually counted and the number recorded as Filaments$_{Side\ 1}$. Exemplary viscose filaments 1010 are shown in FIG. 10. The crenulated surface is shown along with the distinctive ends of the viscose fibers. To prevent counting a filament more than once, each counted filament is "marked" on the image. In like fashion, the number of filaments having a crenulated surface are counted on the low magnification image of the second side of the test sample at the same test region, and the number recorded as Filaments$_{Side\ 2}$. Calculate the Filament Ratio by dividing Filaments$_{Side\ 2}$ by Filaments$_{Side\ 1}$ and record to the nearest 1 unit.

In like fashion, repeat all measurements for a total of 6 replicate test samples. Calculate the arithmetic mean for Filament Ratio obtained for all 6 replicates and report to the nearest 1 unit.

Opacity

Opacity by contrast ratio measurements are made using a 0°/45° spectrophotometer with adjustable apertures capable of making standard CIE color measurements using XYZ coordinates. An example of a suitable spectrophotometer is the Labscan XE (available from Hunter Associates Laboratory, Inc., Reston, Va., or equivalent). Measurements are conducted on a single layer of test material. All testing is performed in a room maintained at a temperature of 23° C.±2.0° C. and a relative humidity of 50%±2% and samples are conditioned under the same environmental conditions for at least 2 hours prior to testing.

Obtain a test sample by removing it from an absorbent article, if necessary. When excising the sample from an absorbent article, use care to not impart any contamination or distortion to the sample layer during the process. The test sample is obtained from an area free of folds or wrinkles, and it must be larger than the aperture being used on the spectrophotometer. Note which side of the test sample is facing (or is meant to face) the wearer during use. This is the side that will face the aperture during the test. Obtain a sufficient quantity of the sample material such that ten measurements can be made on non-overlapping areas of the material being evaluated.

To measure Opacity, calibrate and standardize the instrument per the vendor instructions using the standard white and black tiles provided by the vendor with a 1.2 inch diameter aperture. Set the spectrophotometer to use the CIE XYZ color space with a D65 standard illumination, a 10° observer, 1.2 inch aperture, 1.0 inch area view, and set the UV filter to nominal. Place the wearer-facing side of the test sample over the aperture and ensure that the entire aperture opening is covered by the sample. Place the standard white tile directly against the back side of the sample, take a reading and record the Y value as Y$_{white\ backing}$ to the nearest 0.01 units. Without moving the position of the test sample, remove the standard white tile and replace it with the black standard tile. Take a reading and record the Y value as Y$_{black\ backing}$ to the nearest 0.01 units. Calculate Opacity by dividing the Y$_{black\ backing}$ value by the Y$_{white\ backing}$ value and then multiply by 100. Record Opacity to the nearest 0.1 percent.

In like fashion, repeat for a total of ten measurements on non-overlapping areas of the test sample material. Calculate the arithmetic mean for Opacity obtained from all ten measurements and report to the nearest 0.1 percent.

Tensile Test

The tensile properties of a material are measured on a constant rate of extension tensile tester (a suitable instrument is the MTS Alliance using Testworks 4.0 Software, as available from MTS Systems Corp., Eden Prairie, Minn., or equivalent) using a load cell for which the forces measured are within 1% to 99% of the limit of the cell. All testing is performed in a room controlled at 23° C.±3 C° and 50%±2% relative humidity and test samples are conditioned in this environment for at least 2 hours prior to testing.

To hold the test sample, an identical set of grips are used, with one attached to the lower fixture and the other attached to the upper fixture of the tensile tester. The grips are manual or pneumatic and lightweight to maximize the capacity of the load cell, and they must be wider than the test sample. The grips are constructed in such a way that a single line of gripping force along a line perpendicular to the pull axis of the tensile tester is enabled. The top and bottom grips are mounted in such a way that they are horizontally and vertically aligned.

Obtain the test material by removing it from an absorbent article, if necessary. When excising the test material from an absorbent article, use care to not impart any contamination or distortion to the material layer during the process. The test sample is obtained from an area on the test material that is free of folds or wrinkles. Testing is performed in the Machine Direction (MD) and Cross Direction (CD) of the test material, and test samples are prepared as follows. The dimensions of the MD test sample are such that the length enables a gage length of 51.0 mm (parallel to the longitudinal axis of the absorbent article) with a width of 25.4 mm (parallel to the transverse axis of the absorbent article). The dimensions of the CD test sample are such that the length enables a gage length of 51.0 mm (parallel to the transverse axis of the absorbent article) with a width of 25.4 mm (parallel to the longitudinal axis of the absorbent article). When cutting test samples, ensure that the material is not stretched or distorted. A sufficient number of test samples are prepared such that 5 replicates can be tested in both the MD and CD.

Program the tensile tester for a constant rate of extension uniaxial elongation to break test as follows. Set the nominal gauge length to 51.0 mm ($L_{initial}$) using a ruler traceable to NIST and zero the crosshead. Insert the MD test sample into the grips such that the long side is centered and parallel to the central pull axis of the tensile tester. Raise the crosshead at a rate of 254 mm/min until the test sample breaks, collecting force (N) and extension (mm) data at 50 Hz throughout the test. Return the crosshead to its original location. Construct a graph of force (N) versus extension (mm). Read the maximum peak force (N) from the graph and record as MD Peak Force to the nearest 0.1 N. Read the extension (mm) at the maximum Peak Force from the graph and record as $L_{peak}$ to the nearest 0.1 mm. Calculate MD Elongation at Peak as $[(L_{peak}/L_{initial})*100]$ and record to the nearest 0.1%. In like fashion, repeat the test for the CD test sample, and report CD Peak Force to the nearest 0.1 N and CD Elongation at Peak to the nearest 0.1%

In like fashion, repeat the test for a total of five replicate test samples obtained from the MD and five replicates obtained from the CD of the test material. Calculate the arithmetic mean for MD Peak Force and CD Peak Force, and report each to the nearest 0.1 N. Calculate the arithmetic mean for MD Elongation at Peak and CD Elongation at Peak, and report each to the nearest 0.1%.

Caliper

The caliper, or thickness, of a material is measured as the distance between a reference platform on which the material rests and a pressure foot that exerts a specified amount of pressure onto the material over a specified amount of time. All measurements are performed in a laboratory maintained at 23° C.±2° C. and 50%±2% relative humidity and test samples are conditioned in this environment for at least 2 hours prior to testing.

Caliper is measured with a manually-operated micrometer equipped with a pressure foot capable of exerting a steady pressure of 0.50 kPa±0.01 kPa onto the test sample. The manually-operated micrometer is a dead-weight type instrument with readings accurate to 0.001 mm. A suitable instrument is Mitutoyo Series 543 ID-C Digimatic, available from VWR International, or equivalent. The pressure foot is a flat ground circular movable face with a diameter that is smaller than the test sample and capable of exerting the required pressure. A suitable pressure foot has a diameter of 56 mm, however a smaller or larger foot can be used depending on the size of the sample being measured. The test sample is supported by a horizontal flat reference platform that is larger than and parallel to the surface of the pressure foot. The system is calibrated and operated per the manufacturer's instructions.

Obtain a test sample by removing it from an absorbent article, if necessary. When excising the test sample from an absorbent article, use care to not impart any contamination or distortion to the test sample layer during the process. The test sample is obtained from an area free of folds or wrinkles, and it must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm±1.0 mm per second until the full pressure is exerted onto the test sample. Wait 5 seconds and then record the caliper of the test sample to the nearest 0.01 mm. In like fashion, repeat for a total of five replicate test samples. Calculate the arithmetic mean for all caliper measurements and report as Thickness to the nearest 0.01 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A fluid management layer comprising an integrated, carded, nonwoven having a basis weight of between about 40 grams per square meter (gsm) and about 120 gsm as determined by the Basis Weight method, the fluid management layer comprising a plurality of absorbent fibers, a plurality of stiffening fibers and a plurality of resilient fibers, wherein the absorbent fibers comprise from about 20 percent to about 75 percent by weight, wherein the stiffening fibers comprise bi-component fibers at about 10 percent to about 40 percent by weight, wherein the resilient fibers comprise from about 20 percent to about 40 percent by weight, as determined by the Material Compositional Analysis method, wherein the fluid management layer has a first side and a second side, and wherein there is a higher number of absorbent fibers on the first side or second side versus the other as determined by the SEM method to determine quantity of cellulosic fibers.

2. The fluid management layer of claim 1, wherein the stiffening fibers comprise a dtex of between 4 and 12, as determined by the Fiber Decitex method.

3. The fluid management layer of claim 1, wherein the fluid management layer exhibits an opacity percentage of from between 48.5 to about 70 percent, as determined by the Opacity method.

4. The fluid management layer of claim 1, wherein a ratio of absorbent fibers on the first side versus absorbent fibers on the second side of from about 5:1 to about 1.5:1.

5. The fluid management layer of claim 1, wherein the absorbent fibers on the first side have a different decitex than the absorbent fibers on the second side.

6. The fluid management layer of claim 1, wherein a ratio of absorbent fibers to stiffening fibers by weight percentage is from about 3:1 to about 1.2:1.

7. The fluid management layer of claim 1, wherein a ratio of absorbent fibers to resilient fibers by weight percentage is from about 3:1 to about 1.3:1.

8. The fluid management layer of claim 1, wherein the MD tensile strength is between about 19N to about 50N, as measured via the tensile test method.

9. The fluid management layer of claim 1, wherein the CD tensile strength is between about 5N to about 15N, as measured via the tensile test method.

10. The fluid management layer of claim 1, wherein fibers on the first side of the fluid management layer have a larger decitex than fibers on the second side of the fluid management layer.

11. The fluid management layer of claim 10, wherein a ratio of absorbent fibers on the first side versus absorbent fibers on the second side of from about 5:1 to about 1.5:1.

12. The fluid management layer of claim 10, wherein the absorbent fibers on the first side have a different cross-section than the absorbent fibers on the second side.

13. The fluid management layer of claim 10, wherein the absorbent fiber linear density is from about 1.0 dtex to about 4 dtex.

14. The fluid management layer of claim 1, wherein the stiffening fiber linear density is from about 1.7 dtex to about 12 dtex.

15. The fluid management layer of claim 1, wherein the resilient fiber linear density is from about 4 dtex to about 12 dtex.

16. The fluid management layer of claim 1, wherein the fluid management layer comprises a visual signal.

17. The fluid management layer of claim 1, wherein the fluid management layer comprises a spunlaced nonwoven.

18. An absorbent article comprising a topsheet, a backsheet, and an absorbent core disposed between the topsheet and the backsheet, and a fluid management layer in accordance with claim 1 disposed between the topsheet and the absorbent core, wherein there is a higher number of absorbent fibers on the second side, and wherein the first side is more proximal to the topsheet than the second side.

19. The absorbent article of claim 18, further comprising a visual signal disposed on the first side of the fluid management layer.

20. The fluid management layer of claim 18, wherein the absorbent fiber linear density is from about 1.0 dtex to about 4 dtex.

* * * * *